(12) United States Patent
Forbes et al.

(10) Patent No.: US 8,900,293 B2
(45) Date of Patent: Dec. 2, 2014

(54) MAGNETICALLY-CONTROLLABLE DELIVERY SYSTEM FOR THERAPEUTIC AGENTS

(75) Inventors: Zachary Graham Forbes, Philadelphia, PA (US); Benjamin Biron Yellen, Philadelphia, PA (US); Kenneth Andrew Barbee, Philadelphia, PA (US); Gennady Friedman, Richboro, PA (US)

(73) Assignee: Drexel University, Philadelphia, PA (US)

( * ) Notice: Subject to any disclaimer, the term of this patent is extended or adjusted under 35 U.S.C. 154(b) by 470 days.

(21) Appl. No.: 12/763,925

(22) Filed: Apr. 20, 2010

(65) Prior Publication Data
US 2010/0204674 A1 Aug. 12, 2010

Related U.S. Application Data

(63) Continuation of application No. 11/210,173, filed on Aug. 22, 2005, now abandoned, which is a continuation-in-part of application No. PCT/US2004/011861, filed on Apr. 16, 2004.

(60) Provisional application No. 60/463,505, filed on Apr. 16, 2003, provisional application No. 60/680,833, filed on May 13, 2005.

(51) Int. Cl.
*A61F 2/06* (2013.01)
*A61M 37/00* (2006.01)
(Continued)

(52) U.S. Cl.
CPC ........... *A61L 27/50* (2013.01); *A61F 2210/009* (2013.01); *A61N 1/30* (2013.01); *A61M 37/00* (2013.01); *A61N 2/00* (2013.01); *A61F 2/82* (2013.01)

USPC .................. 623/1.42; 607/9; 600/12; 604/508

(58) Field of Classification Search
USPC ........ 424/423, 1.29; 623/23.73, 18.12, 23.57, 623/1.42; 606/907; 604/508; 607/9; 600/12
See application file for complete search history.

(56) References Cited

U.S. PATENT DOCUMENTS 4,247,406 A 1/1981 Widder et al.
4,269,826 A 5/1981 Zimmerman et al.
(Continued)

OTHER PUBLICATIONS

Arias, et al. "Synthesis and characterization of poly(ethyl-2-cyanoacrylate) nanoparticles with a magnetic core." 2001, J Control Rel.; 77:309-321.

(Continued)

*Primary Examiner* — Paul Prebilic
(74) *Attorney, Agent, or Firm* — Kathryn Doyle; Brian R. Landry; Saul Ewing LLP

(57) ABSTRACT

A magnetic delivery system for delivering a magnetizable particle to a location in a body, the device includes a magnetizable object implanted in the body, wherein the magnetizable object includes a plurality of segments distributed throughout the magnetizable object and wherein the segments are configured to provide a magnetic gradient for attracting the magnetizable particle and an external source of a magnetic field capable of (i) magnetizing the magnetizable particle and (ii) increasing a degree of magnetization of the magnetizable object and thereby creating the magnetic gradient. A drug delivery system including the magnetic delivery system and a magnetizable particle associated with a therapeutic agent and/or a cell. A cell delivery system based on the magnetic delivery system and a magnetizable particle associated with a cell. A method of using the magnetic delivery system for delivery of a therapeutic agent and/or a cell to a targeted location in a body.

37 Claims, 7 Drawing Sheets

(51) Int. Cl.
*A61N 2/00* (2006.01)
*A61L 27/50* (2006.01)
*A61N 1/30* (2006.01)
*A61F 2/82* (2013.01)

(56) References Cited

U.S. PATENT DOCUMENTS

| | | | |
|---|---|---|---|
| 4,345,588 A | 8/1982 | Widder et al. | |
| 4,652,257 A | 3/1987 | Chang | |
| 5,129,877 A | 7/1992 | Gallo et al. | |
| 5,588,962 A | 12/1996 | Nicholas et al. | |
| 5,916,539 A | 6/1999 | Pilgrimm | |
| 5,921,244 A | 7/1999 | Chen et al. | |
| 6,296,604 B1 | 10/2001 | Garibaldi et al. | |
| 6,315,709 B1 | 11/2001 | Garibaldi et al. | |
| 6,364,823 B1 | 4/2002 | Garibaldi et al. | |
| 6,375,606 B1 | 4/2002 | Garibaldi et al. | |
| 6,805,709 B1* | 10/2004 | Schaldach et al. | 623/1.46 |
| 6,808,535 B1 | 10/2004 | Jordan | |
| 7,335,192 B2 | 2/2008 | Keren et al. | |
| 2002/0133225 A1 | 9/2002 | Gordon | |
| 2003/0139801 A1* | 7/2003 | Sirhan et al. | 623/1.15 |
| 2004/0215338 A1* | 10/2004 | Elkins et al. | 623/1.46 |
| 2010/0260780 A1* | 10/2010 | Levy et al. | 424/172.1 |

OTHER PUBLICATIONS

Babincova, et al., "A controlled drug delivery system based on degradable magnetic polymers." Pharmazie, 1996, Pharmazie 51:515-516.
Babincova, et al., "Controlled drug delivery using magnetoliposomes." 1997, Cellular & Molecular Biology Letters, 2:3-7.
Babincova, et al., "High-gradient magnetic capture of ferrofluids: implications for drug targeting and tumor embolization." 2001, Zeitschrift fïr Naturforschung, 56(9-10):909-911.
Bakker, et al. "Comparison of Velocity Profiles for Different Flow Chamber Designs Used in Studies of Microbial Adhesion to Surfaces." 2003, Appl Environ Microbiol. 69(10):6280-7.
Bell et al., "Human sensitivity to weak magnetic fields." 1991, The Lancet, 338(8781):1521-2.
Buemi, et al. "Cell Proliferation/Cell Death Balance in Renal Cell Cultures after Exposure to a Static Magnetic Field." 2001 Nephron 87:269-273.
Consigny, et al., "Use of Endothelial Cells Containing Superparamagnetic Microspheres to Improve Endothelial Cell Delivery to Arterial Surfaces after Angioplasty." 1999, J Vasc Interv Radiol. 10(2 Pt 1):155-63.
De Cuyper, et al. "Magnetoliposomes: Formation and structural characterization." 1988, Eur Biophys J. 15(5):311-9.
Dhanikula, et al., "Localized paclitaxel delivery." 1999, Int J Pharm. 183(2):85-100.
Duch, "Electrodeposited Co—Ni alloys for MEMS." 2002, J. Micromech. Microeng., 12:400-405.
Flanders, "An alternating-gradient magnetometer." 1988, J. Appl. Phys., 63(8):3940-3945.
Flores, "In-vitro blockage of a simulated vascular system using magnetorheological fluids as a cancer therapy." 2002, Eur. Cells and Mater., 3(Suppl. 2):9-11.
Forbes, et al., "An Approach to Targeted Drug Delivery Based on Uniform Magnetic Fields." 2003, IEEE Trans Magn., 39(5):3372-3377.
Forbes, Z.G., Yellen, B.B., Barbee ,K., Friedman, G., Powerpoint presentation entitled An Approach to Targeted Drug Delivery Based on Uniform Magnetic Fields; presented Apr. 2003.
Forrest, et al. "A degradable polyethylenimine derivative with low toxicity for highly efficient gene delivery." 2003, Bioconjug Chem. 14(5):934-40.
Frank, et al. "Methods for magnetically labeling stem and other cells for detection by in vivo magnetic resonance imaging." 2004, Cytotherapy.6(6):621-5.

Fricker, "Drug-eluting stents: Flashy future or flash-in-the-pan?" 2001, Drug Discovery Today 6(22):1135-1137.
Friedlaender, "Particle Buildup on Single Spheres in HGMS." 1981, IEEE Trans. Magn., 17(6)2804-2806.
Friedlaender, "Particle Motion Near and Capture on Single Spheres in HGMS." 1981, IEEE Trans. Magn., 17(6):2801-2803.
Gallo, et al., "Correspondence re: A.S. Liibbe et al., Preclinical and clinical experiences with magnetic drug targeting." 1997, Cancer Res. 57(14):3063-5.
Garas, "Overview of therapies for prevention of restenosis after coronary interventions." 2001, Pharmacology and Therapeutics, 92(2-3):165-78.
Gershlick, et al. "Treating atherosclerosis: local drug delivery from laboratory studies to clinical trials." 2002, Atherosclerosis, 160(2):259-71.
Gomez-Lopera, et al, "Synthesis and characterization of spherical magnetite/biodegradable polymer composite particles." 2001, J Colloid Interface Sci. 240(1):40-47.
Goodwin, "Targeting and retention of magnetic targeted carriers (MTCs) enhancing intra-arterial chemotherapy."1999, J. of Magnetism and Magnetic Materials 194(1-3):132-139.
Goodwin, et al. "Single-dose toxicity study of hepatic intra-arterial infusion of doxorubicin coupled to a novel magnetically targeted drug carrier." 2001, Toxicol Sci. 60(1):177-83.
Gosselin, et al. "Efficient gene transfer using reversibly cross-linked low molecular weight polyethylenimine." 2001, Bioconjug Chem 12(6):989-94.
Hanzlik, et al. "Superparamagnetic magnetite in the upper beak tissue of homing pigeons." 2000, Biometals. 13(4):325-31.
Hehrlein, et al. "Drug-eluting stent: the 'magic bullet' for prevention of restenosis?" 2002, Basic Res Cardiol. 97(6):417-23.
Hilger,et al.. "Evaluation of temperature increase with different amounts of magnetite in liver tissue samples." 1997, Invest Radiol. 32(11):705-12.
Hyeon, "Chemical synthesis of magnetic nanoparticles." 2003, Chem Commun (Camb). (8):927-34.
Igartua, et al. "Development and characterization of solid lipid nanoparticles loaded with magnetite."2002, Int J Pharm. 233(1-2):149-57.
Iino, "Effects of a Homogenous Magnetic Field on Erythrocyte Sedimentation and Aggregation." 1997, Bioelectromagnetics. 18(3):215-22.
Illum, et al. "Development of systems for targeting the regional lymph nodes for diagnostic imaging: In vivo behavior of colloidal PEG-coated magnetite nanospheres in the rat following interstitital administration." 2001, Pharm Res. May 2001;18(5):640-5.
Ito, et al. "Magnetic granules: a novel system for specific drug delivery to esophageal mucosa in oral administration." 1990 Intl Journal of Pharmaceutics. 61(1-2):109-117.
Kato, "Encapsulated drugs in targeted cancer therapy." in Bruck SD (Ed.). Controlled drug delivery. CRC Press, Boca Raton, FL, pp. 190-240, 1983.
Khalafalla, S.E. "Magnetic fluids." Chemtech. Sep. 1975; 540-546.
Kirschvink et al., "Magnetite biomineralization in the human brain." 1992, Proc Natl Acad Sci USA. 89(16):7683-7.
Kirschvink et al., "Magnetite in human tissues: A mechanism for the biological effects of weak ELF magnetic fields." 1992, Bioelectromagnetics. Suppl 1:101-13.
Krotz, et al. "Magnetofection—a highly efficient tool for antisense oligonucleotide delivery in vitro and in vivo." 2003, Krotz, et al. "Magnetofection—a highly efficient tool for antisense oligonucleotide delivery in vitro and in vivo." 2003, Molec Ther. 7(5):700-710.
Krotz, et al. Magnetofection potentiates gene delivery to cultured endothelial cells. 2003, J Vasc Res. 40(5):425-34.
Kumar, "Nano and microparticles as controlled drug delivery devices." J Pharm Pharmaceut Sci. 2000; 3(2):234-258.
Liggins, et al., "Paclitaxel loaded poly(L-lactic acid) microspheres: properties of microspheres made with low molecular weight polymers." 2001, Int J Pharm. 222(1):19-33.
Liu et al. "In-vitro investigation of blood embolization in cancer treatment using magnetorheological fluids." 2001, J. of Magnetism and Magnetic Materials 225:209-217.

(56) References Cited

OTHER PUBLICATIONS

Lonnemark, et al. "Effect of superparamagnetic particles as oral contrast medium at magnetic resonance imaging. A phase I clinical study." 1989, Acta Radiol. 30(2):193-6.
Lubbe, et al., "Clinical applications of magnetic drug targeting." 2001, J Surg Res. Feb. 2001;95(2):200-6.
Mertl, "Magnetic Cells: Stuff or Legend?" 1999, Science. 283(5403):775.
Messai, et al., "Elaboration of poly(ethyleneimine) coated poly(D, L-lactic acid) particles. Effect of ionic strength on the surface properties and DNA binding capabilities." 2003, Colloids and Surfaces B: Biointerfaces. 32(4):293-305.
Messer, et al. "Effect of vascular stent alloys on expression of cellular adhesion molecules by endothelial cells." 2005, J Long Term Eff Med Implants.15(1):39-47 (Jan. 2005).
Minamimura, et al. "Tumor regression by inductive hyperthermia combined with hepatic embolization using dextran magnetite-incorporated microspheres in rats." 2000, Int J Oncol. 16(6):1153-8.
Mitsumori,et al. "Targeted hyperthermia using dextran magnetite complex: A new treatment modality for liver tumors." 1996, Hepatogastroenterology. 43(12):1431-7.
Moore, et al. "The use of magnetite-doped polymeric microspheres in calibrating cell tracking velocimetry." 2000, J Biochem Biophys Methods. 44(1-2):115-30.
Mosbach, et al., "Preparation and characterization (application) of magnetic polymers for targeting of drugs." 1979, FEBS Letters, 102(1):112-116.
Muller, et al. "Cytotoxicity of magnetite-loaded polylactide, polylactidelglycolide particles and solid lipid nanoparticles." 1996, Intl J of Pharmaceut. 138(1):85-94.
Myung, et al. "Electrodeposited Hard Magnetic Thin Films for MEMS Applications." 2000, Proc. Electrochem. Soc., PV, 2000-2029.
Nakamura et al, "Magneto-medicine: Biological aspects of ferromagnetic fine particles."1971, J. Appl. Physics., 42(4):1320-1324.
Ovadia, et al. "Magnetic microspheres as drug carriers: Factors influencing localization at different anatomical sites in the rats." 1983, Isr J Med Sci.19(7):631-7.
Pauser, et al. "Liposome-encapsulated superparamagnetic iron oxide particles as markers in an MRI-guided search for tumor-specific drug carriers." 1997, Anticancer Drug Des. 12(2):125-35.
Plank, et al. "Magnetofection: enhancing and targeting gene delivery with superparamagnetic nanoparticles and magnetic fields." 2003, J Liposome Res. 13(1):29-32.
Plank, et al. "Enhancing and targeting nucleic acid delivery by magnetic force." 2003, Expert Opin Biol Ther. 3(5):745-58.
Plank, et al. "The magnetofection method: Using magnetic force to enhance gene delivery." 2003, Biol Chem. 384(5):737-747.
Plavins, et al., "Study of colloidal magnetite-binding erythrocytes: Prospects for cell separation." 1993, Journal of Magnetism and Magnetic Materials.,122(1-3):349-353.
Quintanar-Guerrero, et al. "Preparation techniques and mechanisms of formation of biodegradable nanoparticles from preformed polymers." 1998; Drug Dev Ind Pharm. Dec. 1998;24(12):1113-28.
Regar, et al. "Stent development and local drug delivery." 2001, Br Med Bull. 59:227-48.
Rudge, et al. "Adsorption and desorption of chemotherapeutic drugs from a magnetically targeted carrier (MTC)," 2001, J Control Release. 74(1-3):335-40.
Ruuge, et al., "Magnetic fluids as drug carriers: Targeted transport of drugs by a magnetic field." 1993, J. Magn. Mag. Mat 122(1-3)335-339.

Sakhnini et al., "Magnetic behavior of human erythrocytes at different hemoglobin states." 2001, Eur Biophys J. 30(6):467-70.
Schenck, "Safety of Strong, Static Magnetic Fields." 2000, J Magn Reson Imaging. 12(1):2-19.
Scherer, F., et al. "Magnetofection: enhancing and targeting gene delivery by magnetic force in vitro and in vivo." 2002, Gene Ther. 9(2):102-9.
Schewe, et al., "Observation of Particle Trajectories in an HGMS Single-Wire System." 1980, IEEE Trans. Magn., 16(1):149-154.
Schwartz, et al. "Drug-Eluting Stents in Preclinical Studies: Recommended Evaluation From a Consensus Group." 2002, Circulation. 106(14):1867-73.
Segre et al., "A. Behaviour of macroscopic rigid spheres in Poiseuille flow Part 1 & 2."1962, J. Fluid Mech., 14(1):115-157.
Senyei, et al., "Magnetic guidance of drug-carrying microspheres." 1978, J. Appl. Physiol., 49(6): 3578-3583.
Sheng et al., "In vitro investigation of a novel cancer therapeutic method using embolizing roperties of magnetorheological fluids." 1999, J. of Magnetism and Magnetic Materials 194(1-3):167-175.
Singla, et al., "Paclitaxel and its formulations." 2002, Int J Pharm. 235(1-2):179-92.
Sousa, et al. "Use of Rapamycin-Impregnated Stents in Coronary Arteries." 2003, Transplant Proc. 35(3 Suppl):165S-170S.
Sullivan, et al. "Development of a novel gene delivery scaffold utilizing colloidal gold-polyethylenimine conjugates for DNA condensation." 2003, Gene Ther. 10(22):1882-90.
Tiefenauer, et al. "In vivo evaluation of magnetite nanoparticles for use as a tumor contrast agent in MRI." 1996, Magn Reson Imaging. 1996;14(4):391-402.
Voltairas et al., "Hydrodynamics of magnetic drug targeting." 2002, J Biomech. 35(6):813-21.
Vyas, et al., "Ligand-receptor-mediated drug delivery: an emerging paradigm in cellular drug targeting." 2001, Crit Rev Ther Drug Carrier Syst. 18(1):1-76.
Wang, et al. "Mechanotransduction across the cell surface and through the cytoskeleton." 1993, Science. 260(5111):1124-7.
Wang,et al. Characterization of the initial burst release of a model peptide from poly(D, L,-lactide-co-glycolide microspheres. 2002, J Control Release. 82(2-3):289-307.
Watarai, et al., "Capillary magnetophoresis of human blood cells and their magnetphoretic trapping in a flow system." 2002, J Chromatogr A. 961(1):3-8.
Widder, et al., "Magnetically responsive microspheres and other carriers for the biophysical targeting of antitumor agents." 1979, Adv Pharmacol Chemother. 16:213-71.
Xia, et al., "Soft Lithography." 1998, Annu. Rev. Mater. Sci.,28:153-184.
Yanase, "Antitumor immunity induction by intracellular hyperthermia using magnetite cationic liposomes." 1998, Jpn J Cancer Res. 89(7):775-82.
Yellen, et al., "Targeted Drug Delivery to Magnetic Implants for Therapeutic Applications." 2005, Journal of Magnetism and Magnetic Materials 293(1):647-654 (May 2005).
Yellen, BB,. Forbes Z.G, Barbee K., Friedman G. Powerpoint presentation entitled "Model of an Approach to Targeted Drug Delivery Based on Uniform Magnetic Fields", presented Oct. 2002.
Zborowski, et al. "Red Blood Cell Magnetophoresis". 2003, Biophys J. 84(4):2638-45.
Zhang, et al., "Surface modification of superparamagnetic magnetite nanoparticles and their intracellular uptake." 2002, Biomaterials. 23(7):1553-61.
Hugh Herr, Ph.D."Prosthetic and Orthotic Limbs," Journal of Rehabilitation Research and Development, 39(3) 11-12 (May/Jun. 2002).

* cited by examiner

2μm
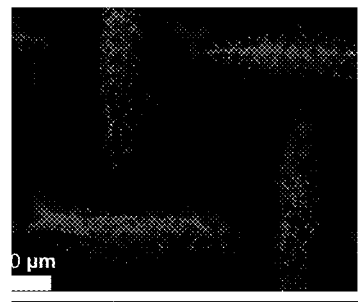
FIG. 5Ai
A Plated Mesh
350nm
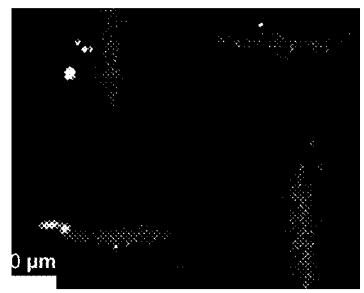
FIG. 5Aii
A Plated Mesh 2μm
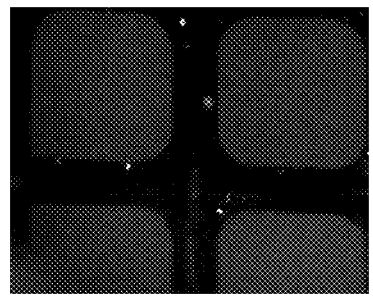
FIG. 5Bi
Unplated Mesh
350nm
FIG. 5Bii
Unplated Mesh

MAGNETICALLY-CONTROLLABLE DELIVERY SYSTEM FOR THERAPEUTIC AGENTS

CROSS-REFERENCE TO RELATED APPLICATIONS

This application is a continuation of U.S. patent application Ser. No. 11/210,173, filed Aug. 22, 2005, now abandoned, which is a continuation-in-part of PCT International Patent Application No. PCT/US2004/011861, filed Apr. 16, 2004 which is entitled to priority under 35 U.S.C. §119(e) to U.S. Provisional Application No. 60/463,505, filed on Apr. 16, 2003 and U.S. Provisional Application No. 60/680,833, filed on May 13, 2005, all of which are hereby incorporated by reference in their entirety herein.

STATEMENT REGARDING FEDERALLY SUPPORTED RESEARCH OR DEVELOPMENT

This invention was made with government support from the National Heart Lung and Blood Institute, Grant No. HL59730 and NSF Grant No. 9984276. The government has certain rights in the invention.

BACKGROUND OF THE INVENTION

1. Field of Invention

The present invention relates to magnetically controllable delivery systems and methods of using thereof to attract and deliver therapeutic agents attached to, or encapsulated within, magnetic particles (i.e., carriers) at selected sites in a body or a subject. More specifically, this invention relates to the use of two sources of magnetic force to deliver therapeutic agents including cells by utilizing magnetizable particles associated with the therapeutic agents.

2. Description of Related Art

The best approach for treating tumors and other localized ailments is to administer drugs only at the site of complication. By delivering the drug locally, the toxicity of the drug to the rest of the body can be reduced while maintaining the desired therapeutic benefit at the site of the ailment. Many drugs developed by the pharmaceutical industry have shown remarkable success during in vitro testing and animal trials, but have yielded undesirable results in clinical trials due to systemic toxicity of the drug to the body. Thus, the ability to deliver large concentrations of drugs locally (i.e., only at the site of the ailment) is of major importance for both the pharmaceutical industry and for clinicians.

However, known drug delivery vehicles are not capable of local delivery of high concentrations of drugs by minimally invasive techniques. This is especially true when repeat dosing is required. The magnetic delivery system described herein overcomes many of these difficulties, and provides a method for concentrating drugs at selected sites in the body with minimal stress on the patient.

Stents are commonly used in a variety of biomedical applications. For example, stents are routinely implanted in patients to keep blood vessels open in the coronary arteries, to keep the esophagus from closing due to strictures of cancer, to keep the ureters open for maintenance of kidney drainage, and to keep the bile duct open in patients with pancreatic cancer. Such stents are usually inserted percutaneously under radiological guidance.

Stents comprise a tube shaped object made of metal (e.g., 316 L Stainless Steel), an alloy (e.g., Nickel-Titanium) or polymer (e.g., polyurethane), in a wide range of physiologically appropriate diameters and lengths, which are inserted into a vessel or passage to keep the lumen open and prevent closure due to a stricture or external compression. General stent design varies in the number of intersections and the interstrut area, the in-strut configuration, and the metal-to-artery ratio. The two different expansion principles for stents are balloon-expansion and self-expansion, and the design types can be categorized into five types: ring, tubular, multi-design, coil, and mesh (Regar et al. Br. Med. Bull. 2001 59:227-48; Hehrlein et al. Basic Res. Cardiol. 2002 97:417-23; Gershlick et al. Atherosclerosis 2002 160:259-71; Garas et al. Pharmacology and Therapeutics 2001 92:165-78).

Stents have been routinely used over the last ten years in percutaneous transluminal coronary angioplasty (PTCA), a procedure for the treatment of severe, symptomatic coronary stenosis (Garas, S. M. et al. Pharmacology and Therapeutics 2001 92:165-178). The PTCA procedure was first introduced in the 1970s as an alternative to coronary-artery bypass surgery for the clearing of coronary vessels blocked by plaque. PTCA has proven to be a much less invasive procedure, with patients able to return to work the week following the procedure, as opposed to the lengthy hospital stay required with bypass surgery (Fricker, J. Drug Discovery Today 2001 6:1135-7). Stents are used extensively in PTCA procedures due to their unique ability to master a major complication of balloon angioplasty ((sub) acute vessel closure), and a superior long-term outcome in comparison to balloon angioplasty (Regar et al. Br. Med. Bull. 2001 59:227-48).

However, in-stent restenosis (the re-closing of the vessel) remains a major limitation, particularly in coronary stenting. Restenosis is generally considered a local vascular manifestation of the biological response to injury. The injury as a result of catheter insertion consists of denudation of the intima (endothelium) and stretching of the media (smooth muscle). The wound-healing reaction consists of an inflammatory phase, a granulation phase, and a remodeling phase. The inflammation is characterized by growth factor and platelet activation, the granulation by smooth muscle cell and fibroblast migration and proliferation into the injured area, and the remodeling phase by proteoglycan and collagen synthesis, replacing early fibronectin as the major component of extracellular matrix. Coronary stents comprise mechanical scaffolding that almost completely eliminates recoil and remodeling. However, neo-intimal growth or proliferation is still a problem. Neo-intimal proliferation occurs principally at the site of the primary lesion within the first 6 months after implantation, a major checkpoint for patient health post-surgery (Regar et al. Br. Med. Bull. 2001 59:227-48). Neo-intima forms during the first week after PTCA and the progress is well under way after 4 weeks, with continued progression over the following months (Hehrlein et al. Basic Re. Cardiol. 2002 97:417-23). This neo-intima is an accumulation of smooth muscle cells within a proteoglycan matrix that narrows the previously enlarged lumen. Its formation is triggered by a series of molecular events including leukocyte infiltration, platelet activation, smooth muscle cell expansion, extracellular matrix elaboration, and re-endothelialization (Regar et al. Br. Med. Bull. 2001 59:227-48).

Three major drug delivery techniques under consideration for the prevention of restenosis are (i) prevention of thrombus formation; (ii) prevention of vascular recoil and remodeling; and (iii) prevention of inflammation and cell proliferation (Garas et al. Pharmacology and Therapeutics 2001 92:165-78). In vitro and in vivo animal model experimentation has shown promise in all three categories, mainly in antiproliferation treatments. However, clinical success has been limited (Garas et al. Pharmacology and Therapeutics 2001 92:165-78), primarily due to systemic toxicity.

Local drug delivery provides limited systemic release, thereby reducing the risk of systemic toxicity. Known techniques for local drug delivery include direct coating of the stent with drug, coating of the stent with a drug-containing biodegradable polymer, and hydrogel/drug coating. Biodegradable stents have also been described (Regar et al. Br. Med. Bull. 2001 59:227-48; Hehrlein et al. Basic Res. Cardiol. 2002 97:417-23; Gershlick et al. Atherosclerosis 2002 160:259-71; Garas et al. Pharmacology and Therapeutics 2001 92:165-78; Schwartz et al. Circulation 2002 106:1867-73; Fricker, J. Drug Discovery Today 2001 6:1135-7). Problems with these technologies, however, include the inflammatory response generated due to large polymer concentrations, the inability to deliver effective concentrations, one-time dosage limitations, and, in the case of the biodegradable stent, mechanical compromise. An additional concern with the polymer-coated drug-eluting stents is limitation of the growth of the cell layer necessary to cover the stent and prevent the bare metal from coming in long contact with the blood, thereby leading to clot formation (Schwartz et al. Circulation 2002 106:1867-73; Fricker, J. Drug Discovery Today 2001 6:1135-7).

The ability to apply forces on magnetic particles with external magnetic fields has been harnessed in various biomedical applications including prosthetics (Herr, H. J. of Rehab. Res. and Devel. 2002 39(3):11-12), targeted drug delivery (Goodwin, S. J. of Magnetism and Magnetic Materials 1999 194:209-217) and antiangiogenesis strategies (Liu et al. J. of Magnetism and Magnetic Materials 2001 225:209-217; Sheng et al. J. of Magnetism and Magnetic Materials 1999 194:167-175). U.S. Pat. No. 4,247,406 describes an intravascularly-administrable, magnetically-localizable biodegradable carrier comprising microspheres formed from an amino acid polymer matrix containing magnetic particles embedded within the matrix for targeted delivery of chemotherapeutic agents to cancer patients. Microspheres with magnetic particles, which are suggested to enhance binding of a carrier to the receptors of capillary endothelial cells when under the influence of a suitable magnetic field, are also described in U.S. Pat. No. 5,129,877.

U.S. Pat. Nos. 6,375,606; 6,315,709; 6,296,604; and 6,364,823 describe methods and compositions for treating vascular defects, and in particular aneurysms with a mixture of biocompatible polymer material, a biocompatible solvent, adhesive and preferably magnetic particles to control delivery of the mixture. In these methods, a magnetic coil or ferrofluid is delivered via catheter into the aneurysm. This magnetic device is shaped, delivered, steered and held in place using external magnetic fields and/or gradients. This magnetic device attracts the mixture to the vascular defect wherein it forms an embolus in the defect thereby occluding the defect.

A model for inducing highly localized phase transformations at defined locations in the vascular system by applying 1) external uniform magnetic fields to an injected superparamagnetic colloidal fluid for the purpose of magnetization and 2) using embedded particles to create high magnetic field gradients was described by inventors (Forbes et al. Abstract and Poster Presentation at the 6th Annual New Jersey Symposium on Biomaterials, Oct. 17-18, 2002, Somerset, N.J.). This work describes the use of uniform magnetic fields in combination with large magnetic particles (greater than 2 micron in diameter) to form chains along the direction of applied field and in turn use this to embolize micro-vessels (50-100 microns in diameter). The use of these magnetizable implants in drug delivery was also described previously by authors Z. Forbes, B. B. Yellen, G. Friedman, and K. Barbee (IEEE Trans. Magn. 39(5): 3372-3377 (2003)).

Known methods and devices for delivery of magnetizable drug or agent-containing magnetic carrier to specific locations in the body rely upon a single source of magnetic field to both magnetize the carriers and to pull them by magnetic force to the specific location. Previous attempts to use magnetic particles in these applications have relied on high gradient magnetic fields produced by magnets external to the body to direct magnetic particles to specific locations (see Flores, 2002; Gallo, et al., (1997); Lübbe, et al., (2001); Mossbach, et al., (1979); Rudge, et al., (2001)). The main disadvantage of this approach is that externally generated magnetic fields apply relatively small and insufficiently local forces on micron and nano-scale magnetic particles, and thus these methods have limited applications.

Chen (U.S. Pat. No. 5,921,244) discloses inserting a magnet (an electromagnet or a permanent magnet) or a plurality of magnets into an opening in a body to attract magnetic fluid/particles. The plurality of magnets is described to be disposed along the longitudinal axis of the magnetic probe. The plurality of magnets actually forms a larger magnet. Chen does not describe using a plurality of sources of magnetic fields or simultaneously creating a far penetrating field and a strong magnetic field gradient, which cannot be accomplished with a single source.

Gordon (U.S. Patent Publication No. US 2002/0133225) describes a device comprising an implant having a magnetic field and a medical agent carried by a magnetically sensitive carrier. The carrier is introduced into the blood flow of the organism upstream from the target tissue, and the carrier and medical agent migrate via the blood flow to the target tissue. Gordon discloses an implant comprising a magnetized material (e.g., a ferromagnetic or a superparamagnetic material). Examples describe making a stent from ferromagnetic materials and magnetized by using an external magnet or made from a magnetized material. Gordon does not disclose optimizing the surface of the implant for providing a stronger magnetic field gradient. Gordon does not describe using a plurality of sources of magnetic fields.

Single source capture methods, however, are at odds with the underlying physics of magnetic particle capture, which depends on the simultaneous imposition of very strong far-reaching magnetic fields and strong spatial magnetic field gradients. The purpose of the far-reaching field is to increase the magnetic moment of individual drug-containing particles in the vicinity of the field to the point of magnetic saturation. Far-penetrating fields are most typically generated with large magnetic sources. However, the force on a magnetized particle also depends on production of strong magnetic field gradients, which are most easily generated with very small magnetic sources. Thus, the ability to simultaneously produce far-penetrating magnetic fields that have strong magnetic filed gradients is very difficult to accomplish with a single source. For this reason, Chen teaches use of relatively large electromagnets implanted in tissue beds to attract magnetic fluid circulating within the blood vessels that are relatively far away, which is a less effective method for capturing magnetic carriers.

The current invention recognizes that the ability to simultaneously produce far-penetrating magnetic fields that have strong magnetic filed gradients is very difficult to accomplish with a single source and offers solutions to this problem. The present invention further differs from previous techniques in that the goal is to deliver therapeutic agents to a desired tissue site without obstructing flow through the blood vessel.

Despite the foregoing developments, there is still a need in the art for improved methods of delivery of therapeutic agents utilizing magnetic forces.

All references cited herein are incorporated herein by reference in their entireties.

BRIEF SUMMARY OF THE INVENTION

Accordingly, the invention provides a magnetic delivery system for delivering a magnetizable particle to a location in a body, the device comprising a magnetizable object implanted in the body, wherein the magnetizable object includes a plurality of segments distributed throughout the magnetizable object and wherein the segments are configured to provide a magnetic gradient for attracting the magnetizable particle and an external source of a magnetic field capable of (i) magnetizing the magnetizable particle and (ii) increasing a degree of magnetization of the magnetizable object and thereby creating the magnetic gradient.

In certain embodiments, the magnetic delivery system further comprises the magnetizable particle located in the body.

In certain embodiments, at least one of the magnetizable object and the magnetizable particle is magnetized only in the presence of the external magnetic field.

In certain embodiments, at least one of the magnetizable object and the magnetizable particle is permanently magnetized.

In certain embodiments, the magnetization of at least one of the magnetizable object and the magnetizable particle is increased in the presence of the external magnetic field.

Further provided is a method of using the magnetic delivery system for delivery of a therapeutic agent, the method comprising providing the external source of the magnetic field, implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent, and providing an external magnetic field by initializing the external source and thereby (i) magnetizing the magnetizable particle and (ii) increasing the degree of magnetization the magnetizable object and thereby creating the magnetic gradient for attracting and advancing the magnetizable particle toward the magnetizable object.

Further provided is a method of using the magnetic delivery system for delivery of a cell to a body, the method comprising providing the external source of the magnetic field, implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent, and administering the magnetizable particle loaded within the cell to the body, providing an external magnetic field by initializing the external source and thereby (i) magnetizing the magnetizable particle and (ii) increasing the degree of magnetization the magnetizable object and thereby creating the magnetic gradient, and attracting and advancing the magnetizable particle toward the magnetizable object using the magnetic gradient and thereby delivering the cell to the location in the body. In certain embodiments of the method, a size of each segment is selected to commensurate with a size of the magnetizable particle such that at least one spatial dimension of each segment does not exceed by more than about 10,000 times at least one spatial dimension of the magnetizable particle.

Methods of administration of magnetizable particle or magnetic cells include but not limited to systemic delivery (e.g., by injection, catheterization, etc).

In a preferred embodiment, the invention provides a magnetizable implant, preferably a stent, for targeting of magnetic therapeutic agents to a selected site of implantation of the magnetizable implant in a subject through creation of a high field magnetic gradient as well as creation of a relatively uniform magnetic field for magnetizing the magnetic therapeutic agents. In the present invention, two magnetic fields are independently produced in order to improve capture efficiency and uniformity of captured therapeutic agent as a coating on the implant, as well as to allow for miniaturization of the implant.

Further, the object of the present invention is to provide magnetizable objects for implantation in a body or a subject and methods for use of these magnetizable objects in delivering a therapeutic agent encapsulated in or dispersed in a magnetic carrier/particle to the implanted magnetizable object. The magnetizable object of the present invention comprises a biocompatible metal or polymeric structural supporting implant coated with or comprising segments of a magnetizable compound. The magnetizable object is specifically designed to produce strong magnetic field gradients through creation of magnetizable features distributed throughout the implant. An exemplary embodiment of a magnetizable object of the present invention is a magnetic stent, the geometry of which produces a strong magnetic field gradient when modified to comprise magnetic or magnetizable segments. In this embodiment, the stent itself preferably comprises a magnetizable compound. In another exemplary embodiment, a magnetizable compound is uniformly coated on the implant, and the magnetized state of the coating is locally segmented through magnetic recording to provide regions of high field gradients distributed throughout the implant. In another embodiment, the magnetizable coating of the implant is etched into a pattern to produce strong local field gradients at desired locations on the implant surface. In yet another embodiment, the structure of a non-magnetic supporting material of the implant creates well-defined magnetized segments in an otherwise uniform coating of magnetic material. The magnetizable compound in the implant may be permanently magnetized or remain magnetized only in the presence of an externally applied field.

Optimization of the segments (i.e., features) of the implant to produce strong magnetic field gradients reduces the penetration of the magnetic field into the surrounding tissue. Thus, in the present invention, in order to magnetize the magnetic carrier of a therapeutic agent to saturation, a second relatively uniform magnetic source is used which can penetrate deep into the selected delivery site and/or tissue of interest. In one embodiment, this second relatively uniform source is applied externally through use of large electromagnets. In another embodiment, the second relatively uniform magnetic source is implanted internally. In this embodiment, the second relatively uniform magnetic source may be separate from the implant or part of the implant that also creates strong magnetic field gradients.

Further, the invention provides a method of delivering an activated cell to a location in a body, the method comprising providing the activated cell comprising a magnetizable particle; providing an external magnetic field; providing an implantable surface having a plurality of magnetizable features characterized by regions of high field gradients, said magnetizable features distributed throughout the implantable surface; advancing the activated cell by influence of the external magnetic field and the high field gradients toward the location in the body and thereby delivering the activated cell.

Magnetic cell delivery is accomplished by the use of the two source method for magnetic drug delivery to magnetizable implantable surfaces. Biological cells, including, but not limited to endothelial and stem cells, are loaded with magnetizable particles (e.g., superparamagnetic nanoparticles) and form magnetic cells. Cells can be isolated from the patients themselves or obtained from maintained cell lines. Magnetizable particles now provide cells with a large collective magnetic moment in the presence of the uniform fields used within this method to deliver magnetic cells to magnetic implants within the body. The cells are then injected into the body by arterial puncture, catheter release, or intravenous injection. The externally applied magnetic field does not serve to direct the cells to the implant. It saturates their magnetic moment, along with the magnetic moment of the implanted magnetizable implant. The high local magnetic field gradients to the magnetic moment and geometry of the implant provide the strong magnetic forces necessary to capture the cells out of blood flow. These cells can serve as a delivery vehicle for magnetic particles loaded with therapeutics or biologics (e.g., drugs, radioisotopes, antibodies, retroviruses, etc) or they can be used in promoting healthy tissue growth for endothelialization of an implant, wound healing, or otherwise needed tissue regeneration.

Magnetic nanoparticles are delivered by endocytosis into cells, which can be then delivered magnetically to implantable surfaces, e.g., stents. These cells can be used as a vehicle for mass transport of drug loaded particles, or as a means to deliver various cell types such as adult or embryonic stem cells, as well as endothelial cells. This invention can be used for wound healing, in vivo engineering of new healthy tissues, targeted delivery of cells loaded with magnetic drug for local targeting of pathologies such as heart disease, cancer, and nervous system disorders, targeting of autologous and al logous cell types for wound healing and in vivo tissue engineering.

BRIEF DESCRIPTION OF SEVERAL VIEWS OF THE DRAWINGS

The invention will be described in conjunction with the following drawings in which like reference numerals designate like elements and wherein:

As shown in FIG. 1A, blood flow through the artery brings a magnetic drug (which is a therapeutic agent associated with a magnetic carrier/particle) in proximity with the implanted stent. As shown in FIG. 1B, as blood flows through the stent, in the magnetic carrier bearing the therapeutic agent is attracted to the segments that have the magnetizable compound. Thus, the drug can be captured on the surface of the segments or in a close proximity to the segments.

FIG. 2A shows the mesh before exposure to the magnetic carriers/particles, and FIG. 2B shows the mesh after exposure to 2.8-micron magnetic carriers/particles.

FIGS. 5A (comprising FIGS. 5Ai and 5Aii) and 5B (comprising FIGS. 5Bi and 5Bii) are fluorescent microscopy images demonstrating a capture of 2 μm and 350 nm diameter magnetic particles on the electroplated 316L Stainless Steel mesh (5A) and unplated mesh (5B) when exposed to magnetic field under 15 cm/s flow velocity at 1% concentration in DI water. Minimal capture was seen on unplated mesh (5B) where a 500 Gauss field was still applied.

DETAILED DESCRIPTION OF THE INVENTION

Figure 1A:
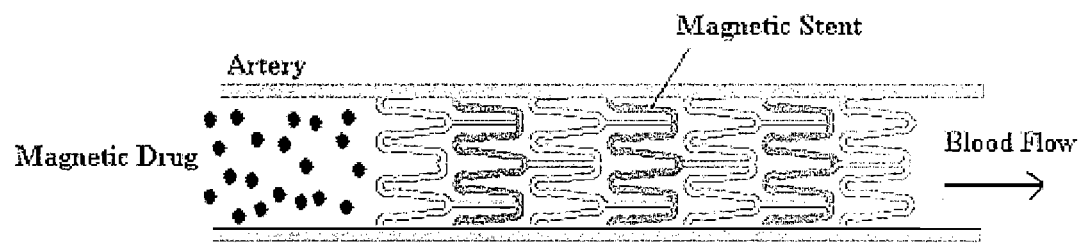
FIGS. 1A and 1B are diagrams of an exemplary embodiment of the magnetizable object of the present invention depicting a magnetic stent as the magnetizable object implanted in an artery. In this embodiment, the magnetizable stent has segments bearing a magnetizable compound which was electro-deposited as a mesh-like structure on some of the struts of the stent. Darkened bars depict the segments (or deposits) of the magnetizable compound which has been deposited on the stent.

The invention was driven by a desire to develop a system capable of targeted delivery of magnetizable particles to a location within a body. Inventors have discovered that magnetizable particles are attracted to regions of the strongest magnetic field gradients and devised a two source system that produces strong and highly localized field gradients inside the body utilizing (1) a magnetizable object implanted in a body as an internal source of a magnetic gradient and (2) an external source of a magnetic field. Unlike the one source systems known in the prior art, this invention utilizes two sources of magnetic influence for targeted delivery of magnetizable particles to areas on the magnetizable object implanted in a body and/or in the near proximity thereto.

Accordingly, the invention provides a magnetic delivery system for delivering a magnetizable particle to a location in a body, the device comprising a magnetizable object implanted in the body, wherein the magnetizable object includes a plurality of segments distributed throughout the magnetizable object and wherein the segments are configured to provide a magnetic gradient for attracting the magnetizable particle and an external source of a magnetic field capable of (i) magnetizing the magnetizable particle and (ii) increasing a degree of magnetization of the magnetizable object and thereby creating the magnetic gradient.

This invention provides the ability to dose the site repeatedly over time with various substances (the same or a different kind) presenting a clear clinical advantage over known delivery systems. The long shelf-life of controlled release spheres and non-drug-coated stents, compared to the expensively sterilized and briefly storable drug-eluting stents is another benefit of this invention.

Further, the magnetic delivery system of the invention can be used together with drug-eluting implants to provide an enhancement for additional doses along the lifetime of the implant. The use of drug eluting implants is limited because of complications related to implantation, cracking of the polymer layer, limited dose size, shelf life, and the fact that they can only provide a single dose. The magnetic delivery system of the invention can be used with endovascular and extravascular implants for treatment of localized tumors. Implants in these cases would have the sole or primary function of facilitating local magnetic drug delivery, and could be implanted by catheter, or in cases where open chest surgery is already required to excise tumors, implanted extravascularly over vessels or organs. This could provide a future option for local chemotherapy at the same site should carcinomas be found to be re-growing during remission.

It should be understood that the benefits of magnetic delivery system of the invention must not come at the cost of increased risk in other arenas, such as chemical tolerance of a magnetic coating or final compositions of polymer and magnetite crystals. It is preferred to utilize FDA approved magnetic or magnetizable particle composites, as well as soft magnetic coatings and magnetic alloys in order to explore the range of manufacturing capabilities that maintain the fundamental essence of the technology such as controllable local delivery of magnetizable particles loaded with a drug and/or a cell to the segments of a magnetizable object. While both soft magnetic coatings and varied alloy composition appear to possess functionality for adapting implants to this magnetic drug delivery system, it is possible that their chemical effects and responses to MRI will differ. As biocompatibility is important in clinical testing, this system provides desired flexibility in the design which makes it much more attractive to the industry.

Regarding MRI, under development is a technology which uses magnetic material to enhance MRI safety and quality (Biophan, MA). This opens the possibility of achieving a balance between such enhancements and the point of magnetization of an implant that would create safety issues relative to movement or torquing of the implant. The current invention provides enough flexibility in the design that the options of patient receiving an MRI would not be compromised. One skilled in the art using the guidance provided in this disclosure would be able to design a magnetic drug delivery system that would not preclude safe and effective MRI procedures for patients receiving the implants in accordance with the invention. Similar concerns can be addressed for other types of treatment or diagnostic methods wherein magnetic interference may be a problem.

Advantages of the invention further include reduced immune cell and capillary concerns regarding the ability of magnetic drug particles to remain in tact to reach their target in blood flow, and highly accurate targeting of rare cell types not available in mass quantities, improved functionality of stem cell therapy.

DEFINITIONS

The term "magnetizable object" as used herein refers to an object capable of creating strong magnetic gradient near its surface (i.e., a local gradient) for attracting magnetizable particles which is implanted in a body. The magnetizable object has a plurality of segments distributed throughout the magnetizable object. The segments are configured to provide a magnetic gradient for attracting the magnetizable particle. This term is used interchangeably with the term "magnetic implant" in the specification.

Magnetizable objects should not be equated with magnetizable particles unless specifically indicated. For example, in certain embodiments, the magnetizable object is formed by a cluster of gradient forming particles, wherein a surface of each gradient forming particle represents a segment of the magnetizable object.

The term "gradient forming particles" as used herein refers to a group or a cluster of particles sized less than 10 micrometers in a diameter each and capable of creating a magnetic gradient for attracting the magnetizable particle. Thus, gradient forming particles play a role of the plurality of segments. Gradient forming particles are made from the same materials as the magnetizable objects made from and can have a variety of shapes, preferably a sphere.

The term "segment" as used herein with relationship to the magnetizable object of the invention refers to an area on the magnetizable object that is characterized by higher magnetization as compared to other areas of the magnetizable object. In other words, in the absence of segments, the magnetizable object is not capable of providing a magnetic gradient (in the presence of magnetic field) that is sufficiently strong to capture magnetizable particles. Thus, a combination of segments with higher magnetization with other areas of lower magnetization on the magnetizable object creates localized high gradients. It should be understood that most surfaces are not ideal and have naturally uneven areas which may magnetize differently. However, for the purposes of this invention, such surfaces are not contemplated as they are not capable of providing sufficiently strong gradient to attract the magnetizable particle.

Non-limiting examples of segments are patterns of indentations and/or ridges of various length, width, depth and shape on the magnetizable object. In preferred embodiments, segments are made by application (e.g., deposition) of a magnetizable compound on a surface of the implant. Referring to a plain view of the magnetizable object such as a stent or a spiral, each coil can serve as a segment. In certain embodiments, the segments comprise patterns of materials with different degrees of magnetization.

By the term "magnetizable compound", as used herein, it is meant a material that conducts magnetic flux strongly. Examples of magnetizable compounds useful in the magnetizable objects (i.e., implants) of the present invention include, but are not limited to, cobalt, iron, iron oxides, nickel, and rare earth magnetic materials and various soft magnetic alloys (e.g., Ni—Co). In one embodiment, the magnetizable compound is magnetized only in the presence of externally applied magnetic fields. Examples of these types of magnetizable compound include, but are not limited to, superparamagnets and soft ferromagnets. In other embodiment, magnetizable compounds known as ferromagnets, which can be permanently magnetized, are used.

The term "coating", as used herein, includes coatings that completely cover a surface, or a portion thereof (e.g., continuous coatings, including those that form films on the surface), as well as coatings that may only partially cover a surface, such as those coatings that after drying leave gaps in coverage on a surface (e.g., discontinuous coatings). The later category of coatings may include, but is not limited to a network of covered and uncovered portions. Coatings can be flat or raised above the surface or embossed on the surface (e.g., a ridge) or it can be in a shape of dots or other shapes creating a pattern. A combination of various coatings can also be used.

Coating can be made from a magnetizable compound (e.g., stainless steel, soft magnetic alloys) and a non-magnetizable compound (a polymer). Selecting the appropriate combination of coating and support materials, it is important that the magnetizable object prepared based on the selection will have a set of segments on its surface that will enable the creation of a localized magnetic gradient. For example, if the support or a surface of the magnetizable object is made from a magnetizable compound, material(s) of the segment can have a higher or a lower degree of magnetization or they can be made from non-magnetizable materials. On the other hand, if the support or a surface of the magnetizable object is made from a non-magnetizable compound, material(s) of the segment must be made from a magnetizable compound.

The term "magnetizable particle" is used interchangeably with the term "magnetic carrier" and the term "magnetic particle" throughout this disclosure.

Exemplary therapeutic agent loaded magnetizable particles comprise a biodegradable matrix (e.g., polymer, protein, DNA) containing, for example, 0-40% by weight therapeutic agent (e.g., drug) and 20% magnetite by weight. Exemplary drugs of low water solubility such as paclitaxel, or commonly used chemotherapeutics like doxirubicin can be used for applications such as coronary artery disease and hepatic cancer, respectfully.

The term "activated cell" as used herein means a cell containing magnetizable particles. This term is used interchangeably with the term "magnetic cell."

The term "endocytosis" means the uptake particles by cells and includes receptor mediated endocytosis.

Magnetizable Object

The magnetizable object of the invention is an implant capable of creating strong magnetic gradient near its surface (i.e., a local gradient) when implanted, such that the magnetic gradient attracts magnetizable particles. The magnetizable object has a plurality of segments distributed throughout the magnetizable object. The segments are configured to provide a magnetic gradient for attracting the magnetizable particle. This term is used interchangeably with the term "magnetic implant" or ":magnetic device" in the specification.

In certain embodiments, the magnetizable object is in the shape of a cylinder, a cylindrical rod, a cube, a cubical rod, a spring, a circular disc, a mesh, a ring, a wire, a sphere or a combination thereof. In certain embodiments, the magnetizable object is a stent, a pacemaker, a catheter, a tube, a vascular graft, an artificial joint, an artificial bone, a prostate seed, an aneurysm coil, a surgical staple, and a suture.

It is also contemplated in this invention that the magnetizable object is does not a have a continuous surface and can be formed from distinct entities such as, for example, a cluster of gradient forming particles, wherein a surface of each gradient forming particle represents a segment of the magnetizable object.

In certain embodiments, a size of each segment is selected to commensurate with a size of the magnetizable particle such that at least one spatial dimension of each segment does not exceed by more than about 10,000 times at least one spatial dimension of the magnetizable particle. In certain embodiments, the size of each segment is selected to commensurate with the size of the magnetizable particle such that at least one spatial dimension of each segment does not exceed by more than about 100 times at least one spatial dimension of the magnetizable particle.

Those skilled in the art would be able to select material for making the magnetizable object such that it would be magnetized in the presence of an external magnetic field as those materials are know or are being developed (e.g., metals, metal alloys and rear earth elements). In certain embodiments, the magnetizable object is made from at least one of materials selected from the group consisting of cobalt, nickel, iron, manganese, samarium and neodymium.

In certain embodiments, the magnetizable object is in a shape of a support made from a metal, a rare earth element, a ceramic, a polymer or a combination thereof. In certain embodiments, the magnetizable object is in a shape of a coating on the support, wherein the coating is made from a metal, a rare earth element, a ceramic, a polymer or a combination thereof. A coating is defined above and is preferably made from a magnetizable compound.

The magnetizable object of the present invention comprises a structural supporting implant made from a biocompatible metal, ceramic, a rare earth element, a polymer or a combination thereof. The magnetizable object of the present invention further comprises a magnetizable compound in a shape of a segment or a coating.

In one embodiment, the magnetizable compound is segmented on the structural supporting implant to provide regions of high field gradients distributed throughout the implant. In another embodiment, the magnetizable compound is uniformly coated on the structural supporting implant, and the magnetized state of the coating is either locally recorded (e.g., embossed and/or indented) to provide regions of high field gradients distributed throughout the implant or uniformly magnetized. In yet another embodiment, the implant itself comprises the magnetizable compound.

In one embodiment, the structurally supporting implant itself is made entirely from alloys of magnetizable compounds.

Figure 1B:
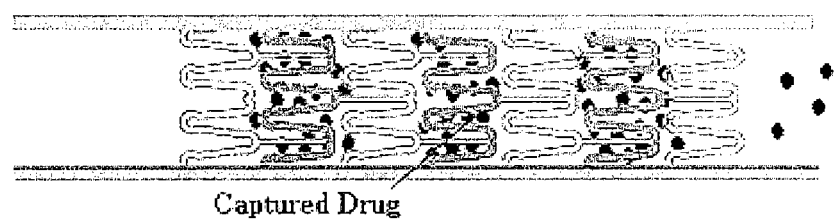
Figure 2A:
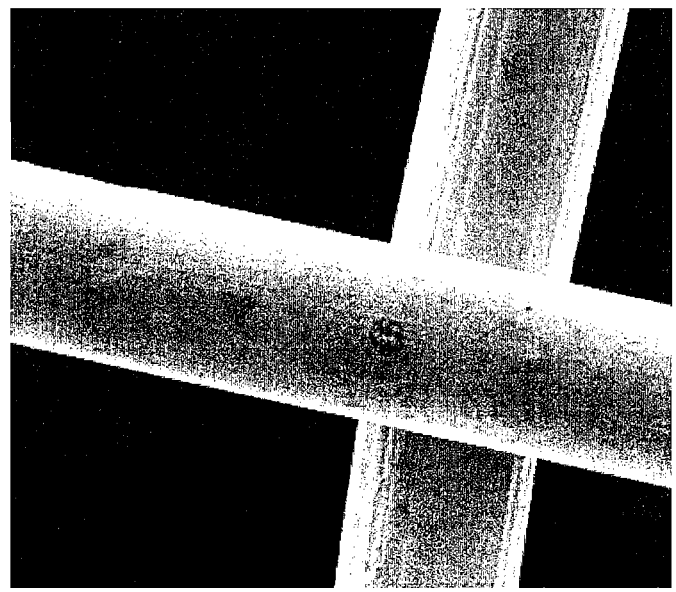
FIGS. 2A and 2B are scanning electron microscopy images of a capture of magnetic carriers/particles (e.g., beads) obtained using a wire mesh electroplated with a magnetizable compound such as Cobalt Nickel (Co—Ni) alloy.
Figure 2B:
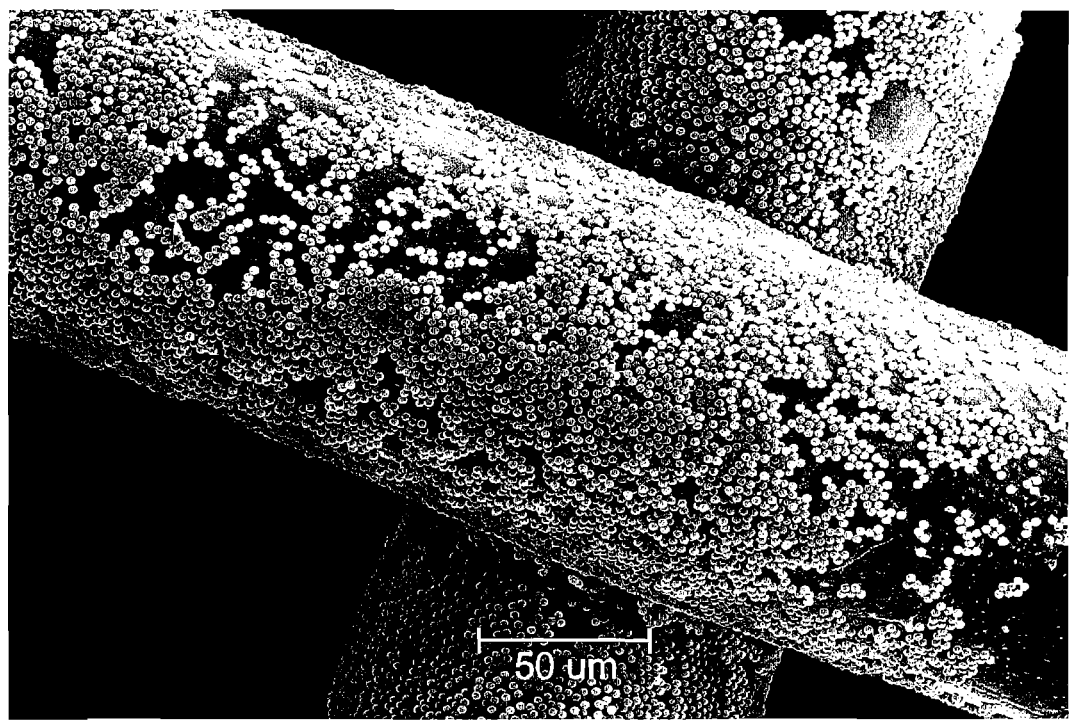

In another embodiment, a layer of magnetizable compound is placed on the structural supporting implant as a coating with a thickness ranging from about 2 nanometers to about 200 microns or in segments. When placed on as segments of magnetizable compound, it is preferred that these segments extend through and around the structural supporting implant from one end of the implant to the other. Similar arrangements include, but are not limited to, multiple rings extending over the implant and a mesh-like structure surrounding the implant such as depicted in FIGS. 1 and 2.

The magnetizable compound can be applied to the structural supporting implant by various methods including, but not limited to, electro-deposition, evaporation and sputtering, and by chemical reactions.

Magnetic particles may not always be uniformly attracted to implants that are simply coated with magnetic material. This is due to the fact that magnetic domains in such coatings are hard to control. Those skilled in the art would be able to select various method of patterning the magnetic coating to control domain patterns in the devices of the present invention without undue experimentation. One method involves laser-assisted electrodeposition of alloys of magnetic metals such as Co, Ni and Fe. In this method, the implant, preferably a stent is used as a cathode during the deposition and a voltage slightly below electroplating threshold is applied. Magnetic material can then be electroplated only in those spots that are exposed to a focused laser beam. Another method for patterning of the implant with the magnetizable compound involves the use of magnetic nanoparticles and nanorods separately prepared. These may either be purchased or made by electroplating into nanotemplates. Magnetic nanoparticles are then deposited onto the implant through a process called dielectrophoresis. In this process the implant is placed into an aqueous solution containing magnetic nanoparticles in between two insulated electrodes. Application of a relatively high frequency (100 KHz-1 MHz) electric field creates strong, high frequency electric field gradients on the implant that attracts the nanoparticles.

Another method for patterning the implant involves recording of magnetic domain pattern on the implant using methods closely related to those that are employed in magnetic information storage devices. One such approach involves laser assisted thermomagnetic recording. In this method, the implant is first uniformly magnetized by a strong external field. Subsequently selected spots are heated by a laser in the presence of a reversed magnetic field. The strength of the reversed field is sufficient to reverse magnetization of heated spots, but insufficient to reverse magnetization of unheated spots. Spots that have been heated by a laser are then magnetized in opposition to the rest of the implant magnetization.

In a preferred embodiment of the device of the present invention, the implant is a stent comprising a metallic tube such as, but not limited to, a corrugated stainless steel tube, coated with a magnetizable compound such as cobalt, iron, iron oxides, nickel, or other rare earth magnetic materials or alloys, followed by a passivating layer of a biocompatible material. In this embodiment, it is preferred that the stent maintain its capability for balloon expansion and complete mechanical integrity so that it is useful not only in selective targeting of therapeutic agents, but also in keeping the lumen into which it is inserted open. Accordingly, this stent-based delivery system, when used in procedures such as PTCA, preserves the beneficial properties of stents (preventing vascular recoil and remodeling) while delivering therapeutic agents, preferably drugs or radionuclides, that inhibit or measure initial thickening, respectively.

The segments of magnetizable compound coated or otherwise deposited on the magnetizable object (e.g., a stent) of the invention provide the stent with the capability to attract arterially injected magnetic carriers including, but not limited to magnetic particles, magnetic liposomes and ferrofluids encapsulating or attached to the therapeutic agent, over the entire stent, thus distributing the therapeutic agent over the entire stent so that possible clogging of the artery and/or stent by deposited therapeutic agent is decreased.

In an alternative embodiment of the device of the present invention, the implant comprises a plurality of biocompatible metal or polymer beads, spikes or pellets wherein at least one segment of each bead, spike or pellet comprises the magnetizable compound. Various means for implanting such a device into the selected site are known and can be selected by one of skill in the art based upon the site of implantation. For example, for implantation into a blood vessel wall, the device may be delivered via a catheter-based system. In this embodiment, it is preferred that the catheter be equipped with a balloon coated with the plurality of implants so that upon expansion of the balloon the implants are lodged into the blood vessel. Alternatively, the balloon can be coated with a plurality of implants which have been modified to further comprise a specific receptor for the endothelial lining which bind to the endothelial lining upon contact. In another embodiment, the device can be implanted by injection of the plurality of magnetizable beads administered to the site of interest and lodged into the tissue by application of external magnetic field gradients. Alternatively, a device of the present invention comprising a plurality of implants can be injected directly into the site of interest by a means similar to a biopsy needle so as to provide a region of high internal magnetic field that attracts magnetic therapeutic agent-containing particles. In these embodiments, it is preferred that the plurality of implants be scattered over the site of treatment so that the therapeutic agent is dispersed over the treatment site and possible clogging of the artery by deposited agent is decreased.

Another aspect of the present invention relates to the use of these devices in the targeted delivery of a therapeutic agent to a selected site in a subject. In this aspect, a device of the present invention is first implanted into a subject at a selected site. The site of implantation in the subject is selected based upon where targeted treatment is desired and the mode of administration for the therapeutic agent.

For example, for PTCA procedures, the treatment site is a coronary artery at a region of stenosis. The therapeutic agent is preferably a drug that is administered intravascularly to prevent restenosis at this site. The implant, preferably a stent, is thus also implanted in the coronary artery at the site of stenosis. In a preferred embodiment, the device of the present invention is implanted by catheterization in accordance with well-known procedures.

While a primary application of these devices is for treatment of cardiovascular disease and/or restenosis, alternative functions for implants of the present invention are envisioned. These include, but are not limited to, treatment of tumors (benign and malignant), bacterial or viral infections, cysts, internal wounds, and anti-rejection treatments for transplant patients. These treatments can be performed by implantation of the device at the mouth of the site of blood supply, or placement of a device with a plurality of implants within or on the site itself, followed by systemic administration of therapeutic agent attached to or encapsulated in a magnetic carrier such as magnetic particles, magnetic liposomes or a ferrofluid.

There are numerous other potential sites of implantation envisioned for a magnetizable/magnetic device of the present invention. It is important to note that in all of these cases, a magnetic carrier such as magnetic particles, magnetic liposomes or a ferrofluid is carrying or bound with the therapeutic agent. These include, but are in no way limited to, the lymphatic system for treatment of swollen or infected glands, and damaged or occluded vessels; in the bile ducts for pancreatic cancer patients; in the ureter or urethra for kidney drainage or kidney/bladder infections; in or on the surface of the larynx, trachea, or lung surface for treatment of respiratory disorders or cancers with the use of an inhalable solution of magnetic particles bound with drug. Further, a device of the present invention placed within the esophagus could be used to capture magnetic particles contained within a viscous creeping solution for treatment of cancers or infection.

In addition, devices of the present invention surgically placed within the brain for local delivery of a therapeutic agent could be used to capture magnetic particles, preferably nanoparticles, with lipid-soluble or other permeability-enhancing coatings to allow targeting of intra-arterial chemotherapeutics. While intra-arterial chemotherapeutics are already practiced in various manners to treat brain tumors, magnetic targeting of such treatments may limit healthy neural tissue exposure to chemotherapy while maximizing dosage levels.

External Source

The external source of a magnetic field of the present invention is capable of (i) magnetizing the magnetizable particle and (ii) increasing a degree of magnetization of the magnetizable object and thereby creating the magnetic gradient. Those skilled in the art using guidance provided in this disclosure will be able to select the proper source and its capabilities without undue experimentation. The preferred external source is an electromagnet.

Magnetizable Particle

In certain embodiments, the magnetizable particle has a diameter of less than 10 micrometers. In certain embodiments, the magnetizable particle has a diameter from about 10 nm to about 1000 nm.

It is also preferred that magnetic carriers such as magnetic particles or magnetic liposomes comprise magnetite. Magnetite is a member of the spinel group with the standard formula $Fe_2O_3$ or $Fe_3O_4$. Magnetite particles to be incorporated in the magnetic particles or magnetic liposomes encapsulating the therapeutic agent are preferably around 10 nm in diameter and are dispersed within the magnetic particle or magnetic liposome to account for 10-50% of sphere volume.

In cases where use of a magnetic carrier comprising microspheres or nanospheres for encapsulation of the therapeutic agent is required, the microspheres or nanospheres preferably comprise a biodegradable polymer, such as poly(lactic acid) PLA and/or poly(lactic-co-glycolic acid) PLGA, which cause minimal inflammatory response upon degradation. As will be understood by those of skill in the art upon reading this disclosure, numerous other biodegradable polymers are known, such as polyhydroxybutyrate and elastomeric poly(ester-amide), which may also be used in these microspheres or nanospheres. Ultimate selection of the biodegradable polymer for encapsulation of the drug is based upon desired degradation times, side effects, and drug conjugation.

In certain embodiments, the magnetizable particle has a diameter from 10 nm to 500 nm. In certain embodiments, the magnetizable particle comprises at least one of materials selected from the group consisting of $Fe_2O_3$, $Fe_3O_4$, FeNi, FePt, Fe, CoNi alloy and optionally a biodegradable polymer. In certain embodiments, the magnetizable particle is in a form of a superparamagnetic colloidal fluid.

In certain embodiments, the magnetizable particle comprises a therapeutic agent and wherein the magnetic delivery system functions as a targeted drug delivery system.

In certain embodiments, the magnetizable particle is loaded within a cell, thereby forms a magnetic cell and wherein the magnetic delivery system functions as a targeted cell delivery system. In certain embodiments, the magnetic cell comprises a therapeutic agent, such that the therapeutic agent is associated with the cell, the magnetizable particle or both and wherein the magnetic delivery system functions as a targeted drug and cell delivery system.

Those skilled in the art should be able to make magnetizable particles utilizing known methods and materials and the guidance of this disclosure.

Therapeutic Agent

The therapeutic agent to be delivered by the method if the invention is encapsulated in, attached to, or dispersed in a magnetic carrier/particle. For example, the therapeutic agent may be encapsulated in magnetic particles including, but not limited to, microspheres and nanospheres or magnetic liposomes. Alternatively, the therapeutic agent may be dispersed in a ferrofluid or in a colloidal fluid. In embodiments wherein the magnetic carrier involves magnetic particles and/or Liposomes, it is preferred that the particles and/or liposomes be less than 10 micrometers in size to prevent clogging of any small arterioles.

Selection of a therapeutic agent to be encapsulated within the magnetic carrier such as magnetic particles or magnetic liposomes or dispersed in a magnetic carrier such as ferrofluid and used with the devices of the present invention is dependent upon the use of the device and/or the condition being treated and the site of implantation of the magnetizable device. For example, multiple therapeutic agents have been experimented with and tested for prevention of restenosis following PTCA and any of these can be used with the stents of the present invention. Some examples of such therapeutic agents include, but are not limited to, antiplatelet agents such as aspirin, glycoprotein receptor antagonists, and cilostazol for prevention of thrombus formation by interfering with platelet aggregation; anticoagulants such as heparin, hirudin, and coumadin for prevention of thrombus formation by blocking the coagulation pathway; calcium channel antagonists for reducing vascular recoil and remodeling; growth factor inhibitors, such as trapidil, an inhibitor of PDGF; immunosuppressants such as Rapamycin (Sirolimus; Rapamune®); anti-inflammatory agents; and anti-proliferation agents such as Actinomycin D (Cosmegen®), Estrogen (Estrodiol®), and Paclitaxel (Taxol®). Thus, for PTCA procedures and tumor treatments using a magnetizable stent of the present invention, a preferred therapeutic agent for encapsulation may be Actinomycin D, Rapamycin or Paclitaxel. Other therapeutic agents that can be administered, include, but are not limited to radioactive materials, gene vectors, genetically modified viruses such as retroviruses, and living cells, such as endothelial cells, that are attached to magnetic particles. The ability to attract endothelial cells to the implant will greatly decrease the time it takes to form an endothelial layer on the stent, and may inhibit the growth and migration of smooth muscle cells that are largely responsible for the neo-intimal growth.

Magnetically targeted therapeutic agent delivery achieved through use of the present invention allows for reduced initial inflammation response often experienced in clinical tests of polymer/drug-coated stents, as the amount of polymer necessary for targeted delivery can be reduced. In addition, since the magnetic vehicles are deliverable via arterial injection, minimally invasive means for delivery of the therapeutic agents at selected times can be used. Thus, in a procedure such as PTCA, a therapeutic agent may not need to be delivered until sufficient time has elapsed for endothelium growth over the stent. Further, multiple doses of the therapeutic agent or combinations of therapeutic agents can be administered.

In some embodiments, the device of the present invention and/or magnetic carrier of the therapeutic agent may require magnetization just prior to, during or following administration of the therapeutic agent. In these embodiments, the device and/or magnetic carrier of the therapeutic agent is magnetized by a magnetic field applied externally to the subject.

The utility of the devices of the present invention in targeting a therapeutic agent to the site of their implantation is based upon obtaining an attractive magnetic force upon the injected magnetic carrier of the therapeutic agent that overcomes the drag resistance in moving towards the wall. The magnetic force can be optimized by using a device that contains a plurality of magnetic features, producing strong magnetic field gradients that pull the therapeutic agent encapsulated or attached to the magnetic carrier to desired locations on the surface of the implant of the device. The implant of the device is designed to be in direct or proximal contact with the transporting medium for the therapeutic agent so that the therapeutic agent-containing magnetic carrier will be attracted most strongly. For example, in one embodiment as depicted in FIGS. 1A and 1B, the transporting medium is blood of a blood vessel that has been injected with a colloidal solution of therapeutic agent-containing magnetic particles. In another embodiment, the transporting medium is that of an aerial passageway that has been exposed to a gaseous solution of therapeutic agent-containing magnetic particles in the form of a nasal spray or inhalation. In yet another embodiment, the transporting medium comprises lymphatic or cerebrospinal fluid that has been injected with therapeutic agent-containing magnetic particles that are attracted to a device of the present invention in the lymph nodes or brain.

Figure 3:
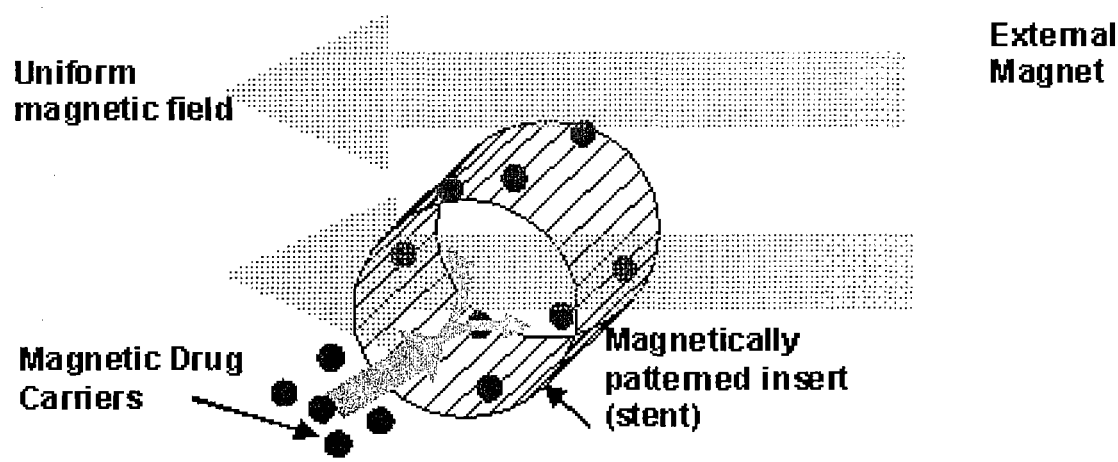
FIG. 3 is a schematic illustration of the preferred embodiment of the magnetic delivery system of the invention.
Figure 4A:
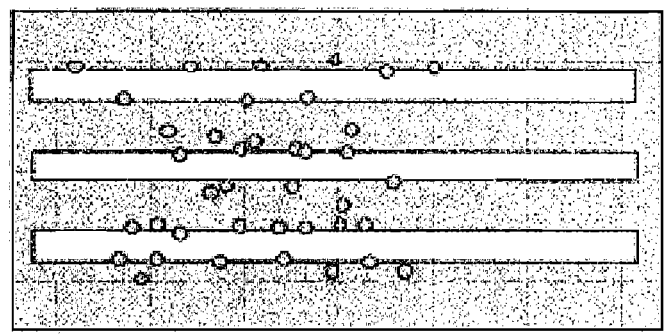
FIG. 4A is a schematic illustration of a top view of microchannels having walls seeded with magnetic particles.
Figure 4B:
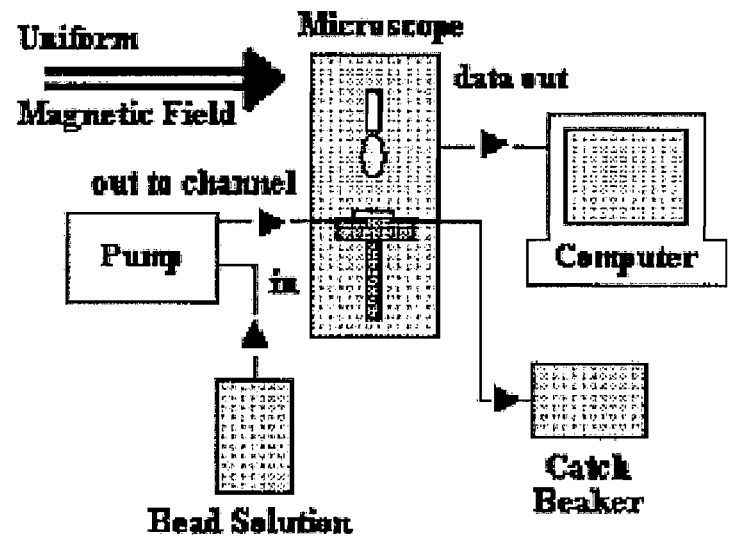
FIG. 4B is a chart depicting a flow of micro-particle solutions through micro-channels shown in FIG. 4A.
Figure 6A:
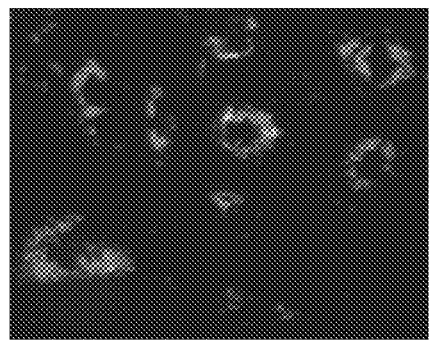
FIG. 6A); confocal image of nuclear stained endothelial cells with internalized magnetizable nanoparticles (top right.
Figure 6B:
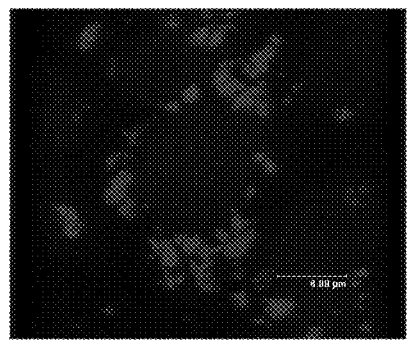
FIG. 6B); magnetic endothelial cells captured to the wires of a magnetized stent mesh (bottom left and right, FIG. 6C and FIG. 6D, respectively).
Figure 6C:
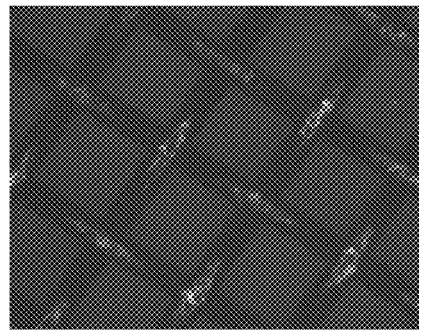
FIG. 6, comprising FIGS. 6A through 6D, includes images of endothelial cells with internalized magnetic nanoparticles: vascular endothelial cells with internalized fluorescent magnetic nanoparticles (top left.
Figure 6D:
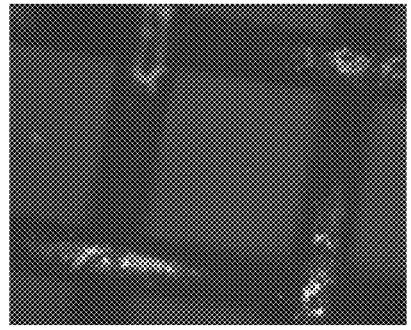

In a preferred embodiment of the invention, high magnetic field gradients within the body are applied to the magnetizable particle which is in a form of an injected superparamagnetic colloidal fluid carrying a therapeutic agent with the aid of uniform magnetic field created by the external magnet toward a target, an endovascular implant (e.g., a stent). The design of the magnetizable object involves patterning the surface of endovascular implants with a soft magnetic coating capable of producing high local magnetic field gradients within the body. A conceptual diagram of the preferred embodiment can be found in FIG. 3.

In the preferred embodiment of the invention, the magnetic delivery system is used for the treatment or prevention of coronary restenosis following angioplasty. The magnetic delivery system of the invention is a viable alternative or enhancement to drug-eluting stents, offering increased control of dose size, the ability to treat a site repeatedly, and a wide array of applications for treatment of other pathologies.

As described in detail below, the magnetic delivery system utilizing micron and sub-micron scale magnetic particles for site-specific delivery of pharmaceuticals and magnetic cells is described based on the theoretical and experimental models (e.g., parallel plate and pipe flow analysis, and cell culture models).

In the preferred embodiment, the present invention is used for treatment and prevention of coronary restenosis. The magnetizable object is in a shape of a stent as described below. The magnetic delivery system will operate by first implanting the stent at designated sites in the cardiovascular system, and then attracting injected or otherwise administered doses of magnetically susceptible drugs as magnetizable particles to the sites of the implant the with the aid of the external magnetic field and magnetic field gradient created by the implant (i.e., stent). In vitro experiments demonstrated that magnetizable particles were attracted to regions of the strongest magnetic field gradients.

Ability of local magnetic field gradients to trap magnetic particles can be demonstrated based on computational models. Adaptation of these models to the analysis of a magnetizable steel mesh (i.e., the magnetizable object) provided insight for implant magnetization, external magnetic field parameters, particle and vessel sizes, as well as preliminary dose concentrations for beginning in vitro flow simulations.

Determination of the attractive magnetic forces in the preferred embodiment that is necessary to capture agent-containing magnetic particles was achieved by modeling the force on a single magnetic particle in blow flow due to the magnetic field from a bar of magnetic material as follows.

A rigid sphere transported along in Poiseuille flow through a tube has been shown to be subject to radial forces which tend to carry it to a certain equilibrium position at about 0.6 tube radii from the axis, irrespective of the radial position at which the sphere enters the tube (Segre, G. and Silberberg, A. J. Fluid Mech. 1962 14:136). Further, it has been shown that the trajectories of the particles are portions of one master trajectory, and that the origin of the forces causing the radial displacements is in the inertia of the moving fluid (Segre, G. and Silberberg, A. J. Fluid Mech. 1962 14:136).

Before the effects of multiple particles inside a lumen coated three dimensionally with magnetic segments can be modeled, it must first be ensured that were there only one particle, and one bar of magnetic material, that the magnetic attraction would be strong enough that in fluid flow the particle would be able to overcome the drag resistance and attach to the implant. Accordingly, the magnetic force has been modeled as Fz, the force in the z direction on a particle by a bar of magnetic material directly placed along the lumen of the vessel. From basic electromagnetic theory it is known that the force on a magnetizable spherical bead in an external magnetic field is given by Equation 1.

$$\vec{F} = \mu_0 (\vec{m} \cdot \nabla) \vec{H}. \qquad \text{Eq. 1}$$

$$\vec{m} = \frac{3\chi}{\chi + 3} V \vec{H} \qquad \text{Eq. 2}$$

In Equations 1 and 2, $\mu_0$ is the magnetic permeability of free space, H is the total external magnetic field, m is the magnetic moment of the particle attracted to the implant, V is the volume of the particle, and x is the magnetic susceptibility of the particle. As can be seen from Equation 1, the force is directly proportional to both the magnetic moment of the particle and the magnetic field gradient. The trajectory of the particle is computed numerically according to Eq. 3 by modeling the movement of the particle towards the wall in a velocity flow field. A particle is captured if its trajectory terminates on the site of the implant:

$$\Delta z = \frac{F_z}{6 \pi \eta a v_x} \Delta x \qquad \text{Eq. 3}$$

Using values ranging from extreme to moderate to account for varying inducible magnetic field strength, particle size, and blood flow velocity, simulations have shown that for a variety of different physiologically significant parameters, $F_z$ can indeed overcome the vertical drag resistance. These equations must then be modeled based around a circumference equally spaced with magnetic segments, and a fluid containing multiple magnetic particles.

In vitro experiments of various kinds have been conducted which demonstrate the utility of devices of the present invention in drug delivery. In one set of experiments, a 316L stainless steel stent was coated with cobalt by electro-deposition. This mesh was then placed within a flow chamber, and magnetic particles were flown through the chamber at varying velocities to assess the capability of the mesh to attract them. Aggregation of magnetic particles on the magnetic stent was increased as compared to a non-magnetic stent.

In another set of experiments, magnetizable beads were embedded in microchannels and magnetic microspheres were injected into the channel under applied magnetic field in order to determine if the embedded beads could capture the microspheres. Again the magnetic microspheres aggregated on the magnetized embedded beads.

Experiments using microfabricated fluidic channels were carried out to show a uniqueness of using the magnetizable stent with the surface-modified nanoparticles. Microfluidic channels of various sizes (50×50, 100×100, 500×500 µm cross-section) were fabricated in polydimethyl siloxane (PDMS). The walls of the micro-channels were seeded with superparamagnetic/latex composite microparticles (5 µm diameter) (See Forbes Z G, Yellen B B, Barbee K A, Friedman G, An Approach to Targeted Drug Delivery Based on Uniform Magnetic Fields, IEEE Transactions on Magnetics, 39 (5): 3372-3377, (2003)). Top views of the micro-channels and of the entire experimental set-up are schematically illustrated in FIG. 2. Various concentration solutions of commercially available magnetic particles of various sizes (1 µm, 3 µm, 5

μm, 7 μm) were observed to flow in the channels while applying external relatively uniform magnetic field varied up to 300 Oe (0.03 Tesla). When no magnetic field is applied, magnetic particle solution flows freely. When the applied magnetic field exceeded 30 Oe aggregation of particles is observed. Stronger fields lead to faster and more pronounced attraction of magnetic particles in solution toward the walls. In lower concentration particle solution, particle chains attracted to the walls form relatively slowly (10 s of seconds). In higher concentration particle solution, aggregation of particles on the micro-channel walls occurs very quickly. Examples of aggregation of magnetic carriers in the micro-channels are shown under various flow conditions and fields were observed.

The possibility of making stents that could attract magnetic particle carriers under similar conditions was also confirmed using the technique. Commercially available (e.g., Cord is Corp) stainless steel stents were first confirmed not to attract commercially available magnetic particles (100 nm, 1 μm and 5 μm diameter). A basic set-up for electroplating these stents was developed and stents were coated with 1 μm thick layer of cobalt. The cobalt coated stents were placed into the magnetic particle solution and strongly attracted magnetic particles when a permanent magnet applying a relatively uniform field was placed above the stents. The cobalt coated stents remained covered by the magnetic particles even after washing.

Explanation of Basic Principles of the Proposed Method

The magnetic force dragging isolated magnetic carriers toward the stent is:

$$\vec{F}=(\vec{M}\cdot\nabla)\vec{B} \quad (1)$$

where the magnetic moment $\vec{M} \approx \lambda \vec{B}$ of the drug carrying particle is approximately proportional to the total field $\vec{B}$ up until saturation which occurs for most nanoparticles in the range of about 600 Oe (0.06 Tesla). The total field $\vec{B}=\vec{B}_{ext}+\vec{B}_{stent}$ experienced by the magnetic carriers consists of contributions due to the stent and due to the external magnet. However, while the field of the external magnet is much larger than the field of the stent, it is largely uniform ($\nabla \vec{B}_{ext} \approx 0$). The stent, on the other hand, produces very large gradients near itself because of the presence of very small magnetized features on it. Thus, from (1) and from above arguments, the force on magnetic drug carriers can be approximately written as $$\vec{F} \approx \lambda (\vec{B}_{ext} \cdot \nabla) \vec{B}_{stent} \quad (2)$$

The above formula makes it clear that forces capturing drug carriers are maximized when a strong external uniform magnetic field is superimposed on a field produced by an insert with tiny features maximizing field gradients. Inventors believe that this can not be achieved by a single external magnet. Numerical simulations have been carried out to study efficiency of magnetic carrier capture by magnetized inserts. These simulations have indicated that capture of magnetic carriers as small as 100 nm is feasible with stents that are patterned with magnetized features that are 2-3 μm in diameter and about 200-500 nm in thickness.

It was observed that magnetic carriers may not always be uniformly attracted to stents that are simply coated with magnetic material. This is due to the fact that magnetic domains in such coatings are hard to control. This invention provides several means of patterning the magnetic coating to control domain patterns.

One embodiment involves laser assisted electrodeposition of alloys of magnetic metals such as Co, Ni and Fe. Stents will be used as cathodes during the deposition and voltage slightly below electroplating threshold will be applied. Magnetic material can then be electroplated only in those spots that are exposed to a focused laser beam.

Another approach to stent patterning involves the use of magnetic nanoparticles and nanorods separately prepared. These may either be purchased or made by electroplating into nanotemplates. Magnetic nanoparticles (e.g., ferromagnetic) will then be deposited onto the stents through a process called dielectrophoresis. In this process the stent will be placed into an aqueous solution containing magnetic nanoparticles in between two insulated electrodes. Application of a relatively high frequency (100 KHz-1 MHz) electric field will create strong high frequency electric field gradients on the stent that will attract the nanoparticles.

Another approach involves recording of magnetic domain pattern on stents using methods closely related to those that are employed in magnetic information storage devices. One such approach will involve laser assisted thermomagnetic recording. In this method the stent is first uniformly magnetized by a strong external field. Subsequently selected spots are heated by a laser in the presence of a reversed magnetic field. The strength of the reversed field is sufficient to reverse magnetization of heated spots, but insufficient to reverse magnetization of unheated spots. In the end, spots that have been heated by a laser, will be magnetized in opposition to the rest of the stent magnetization.

The design of the magnetizable object of the invention (i.e., magnetic implant) began with the selection of stent-simulating materials of different geometries, mesh sizes, and metallic content, suitable for in vitro flow experimentation. In preferred embodiment, stainless steel materials ranging from 316 (316L SS) to 302 (302 SS) grades were chosen, in grid-like mesh geometries, as well as in the form of a compression spring. A soft magnetic alloy of Cobalt-Nickel was selected as a convenient material for increasing the saturation magnetization of the materials, while retaining a very low state of magnetization in the absence of the externally applied magnetic field. An electroplating setup was developed utilizing a cobalt anode, borate bath containing scaled concentrations of cobalt and nickel, and controlled by a potentiostat. By combining the use of very weakly magnetic materials (316L SS) and highly magnetic materials (302 SS) with varied plating heights of soft magnetic alloy, flow experiments were conducted to determine the scalability of magnetic capture over a range of saturation magnetizations. Two flow systems were used to test the capture of magnetic particles onto the wires of model stent materials. The first system employed was a parallel plate flow chamber (PPFC) adaptable to various channel heights and capable of sustaining high volumetric flow rates needed to obtain physiologically significant flow velocities. These experiments provided qualitative results from fluorescent microscopy that validated model predictions that magnetic particles could be captured using the proposed design. The system was validated for particle sizes ranging from 130 nm to 2 μm in diameter, but optimized for 350 nm and 2 μm diameter superparamagnetic particles stained with rhodamin for nile red fluorescence. A characteristic set of experimental data is shown in FIGS. 5A and 5B. These particles were tested and validated for magnetic capture to both 316L and 304 steel meshes, magnetic capture through layers of silicone in order to simulate scar tissue, capture of particles concentrated in porcine blood, and for a range of dose concentrations and volumes.

The second system for flow analysis of the proposed design utilized three-dimensional implants placed within a pipe flow system. Large vessel scaled implants molded from 304 grade steel into 5 mm diameter tubes, as well as 3 mm diameter 302 grade steel compression springs were chosen for testing. These materials maintain a much higher inherent saturation magnetization due to their alloy content, but were also electroplated with various heights of a soft magnetic alloy (e.g., Co—Ni alloy) to examine capture over a range of magnetic properties. The pipe flow analysis also allowed to analyze uncaptured magnetic particles from a single dosage pass using a MicroMag Alternating Gradient Magnetometer (AGM) (Princeton Measurements, NJ). AGM analysis provided capture efficiency percentages, as well as insight into numerical capture capabilities and its variance with dose concentration and material magnetization. A skilled in the art would be able to use these data and guidance provided herein in selection of system parameters (e.g., materials, segments' design, etc.) for applications in vivo without undue experimentation.

Further, the magnetic delivery system was tested for biocompatibility. While the risks of the use of Cobalt-Nickel coatings and magnetite-based magnetic particles can be further studied in vivo, prior art literature gave insight into tissue tolerance. Experiments were conducted to examine any effects on the growth, morphology, and behavior of endothelial cells as a non-limiting example due to the magnetic field gradients of the wires of an electroplated mesh as the magnetizable object. It was found that endothelial cells not only survived the delivery of a high concentration of magnetic particles to cultures, but were actually found to compartmentalize the particles into the cell. The endothelial cells with internalized magnetic particles (i.e., magnetic cells) maintained normal growth, morphology, and behavior and were captured magnetically to mesh surfaces. Images of magnetic cells are shown in FIG. 6.

It was discovered that endothelial cells were able to tolerate magnetic gradients when grown in the presence of a magnetically plated mesh. Further, when cells came in contact with delivered magnetic particles, cells were able to compartmentalize and uptake the particles. These cultures were also found to attach, spread, and divide at rates consistent with control cultures, and to respond to fluid shear stimulation. Magnetic endothelial cells were also successfully delivered magnetically to the surface of magnetic mesh, both in static culture as well as in high flow rate in the parallel plate flow chamber. Significant numbers of these magnetic endothelial cells were able to survive and grow, even after exposure to such potentially traumatic magnetic forces. These results demonstrate that magnetic cells can be used as delivery vehicles for a drug associated with a cell or a magnetic particle, as well as for delivery of cells to a desired location in the body.

In a preferred embodiment, magnetizable nanoparticles were delivered by endocytosis into cells, which can be then delivered magnetically to implantable surfaces, e.g., stents. These magnetic cells can be used as a vehicle for mass transport of drug loaded particles, or as a means to deliver various cell types such as adult or embryonic stem cells, as well as endothelial cells. Experiments conducted with magnetizable nanoparticles and BAEC cells are described in detail below.

The implant material selected for biocompatibility studies was the woven, 316L stainless steel wire mesh (140 µm wire diameter, 400 µm apertures.) This particular material was selected due to its large strut spacing, and extremely low magnetization. As a result, a large difference in response to applied magnetic fields, and subsequently in capture ability, can be compared between a virtual non-magnetic 316L mesh and a CoNi electroplated 316L mesh.

Because of the likely chemical reactivity of the CoNi coating to cells and culture medium, and in order to provide a "level playing field" on which cells could grow and easily be studied, poly(dimethyl siloxane) (PDMS) (Dow Corning, MI) was used to passivate the mesh. Depending on the desired cover slip size (0.25 mm thick, ranging from 5 mm to 25 mm in diameter in the below listed experiments), a volume of PDMS and curing agent (10:1 polymer to curing agent mass ratio) was dropped onto the glass cover slip. The slip was placed by vacuum upon a wafer spinner at the micro-fabrication facilities of the Drexel University Clean Room, and was spun for an appropriate period (5 to 25 seconds depending on the size of the slip) to obtain an even layer of 150 µm of PDMS.

A 5 mm diameter circular punch-out of mesh (at 140 µm thickness) was then dropped on top of the PDMS layer, sinking into the polymer. The preparation was then cured under vacuum at room temperature overnight, and measured with digital calipers to verify height. This creates a roughly 10 µm tall boundary layer between the mesh and the cell culture surface, and while not identically physiologically relevant, provides an excellent working model for studying endothelial cell cultures in close proximity to magnetic gradients, as well as for endothelial cells with internalized magnetic particles in close proximity to magnetic forces when an external field is applied.

Spherotech (Spherotech, IL) magnetic particles were selected for all pipe flow experiments. Spherotech magnetic particles were 20% $\gamma$-$Fe_2O_3$ magnetite by weight, labeled with nile red fluorescent pigment and had a nominal diameter of 350 nm with approximately 10% variance in size. Particles come in 2 mL water solutions concentrated at 1% w/v or $4.8 \times 10^{11}$ particles/mL. These particles have a carboxylate per $nm^2$ of surface area, which can be used as a linker for therapeutics such as peptides, antibodies or other biomolecumes.

Bovine aortic endothelial cells (BAECs) were selected as a culture model. These cells were previously isolated by standard technique at the University of Pennsylvania. All experiments were performed at low-passages (<10). Cells were routinely cultured in low glucose DMEM (Sigma, Mo.) supplemented with 10% Qualified Heat inactivated Fetal Bovine Serum (Sigma, Mo.) and 1% 2.5 mM L-glutamine (Sigma, Mo.). After expansion of the culture using 100 µg/mL streptomycin (Sigma, Mo.), and 100 U/mL penicillin (Sigma, Mo.) per 500 mL batch of medium, it was determined that BAECs could be cultured with ease without the use of antibiotics or antimycotics, and were removed from future batches of culture medium.

Cells were routinely cultured in 75 $cm^2$ flasks in a Fisherbrand cell culture incubator at 37° C. and 5.0% $CO_2$ (Fisher, IL). In preliminary experiments determining the preparation of mesh for culturing, the BAECs were shown to grow poorly on silicone and glass surfaces, and when these surfaces were treated with coated with a 1% Rat Tail Type I Collagen (Sigma, Mo.), cells grew robustly, maintaining a growth rate and visible morphology alike to BAECs cultured in T75 flasks.

5 mm punch-outs of magnetic and non-magnetic mesh were prepared, and treated with PDMS as described above. Prior to use, each of the 6 cover slips (25 mm diameter×0.25 mm thick, 3 with magnetic mesh, 3 with non-magnetic mesh) were washed with soap and water, and rinsed thoroughly. Following cleaning, each mesh was placed in a glass Petri dish within a laminar flow hood, and soaked in 70% ethanol for 30 minutes. After 30 minutes, all ethanol was aspirated, and the cover slips were allowed to dry for 20 minutes.

Two separate 6-well plates were obtained (one for magnetic mesh, the other for non-magnetic mesh), and 3 slips of each experimental group were placed in each. A preparation of 1% by volume Rat Tail Type I Collagen (Sigma, Mo.) in Phosphate Buffered Saline (Sigma, Mo.) was used to add 150 µL to each well. After 30 minutes, the collagen solution was aspirated, the slips rinsed twice with an equal volume of PBS, and allowed to dry for 10 minutes within the laminar flow hood.

BAECs, routinely cultured as described above, were then seeded to each cover slip at 1:2 split ratio (adjusted to $cm^2$ growth area). 3 cm long by 0.5 cm tall by 0.5 cm wide pieces of neodymium permanent magnets were placed under each well, for both non-magnetic and magnetic mesh, and separated by plastic spacers. These pieces applied an approximately 500 Gauss magnetic field at the center of the mesh as measured by a handheld Gaussmeter (Lakeshore Cryotronics, OH). These magnets were kept in place, under the wells, and placed in the cell culture incubator for 30 minutes while cells were allowed to attach to the surface of the collagen-coated PDMS. 30 minutes was selected as a modest period for which a magnetic drug delivery injection may be performed, saturating the magnetic moment of the material for that period. At the conclusion of 30 minutes, the magnets were removed and the samples were left in culture, and imaged by phase contrast at 24 hours.

Magnetizable particles uptake into or chemical attachment on to cell cultures has been used as a means of mechanically stressing cells (Wang, et al., 1993), and also considered as a means for cellular localization (Consigny, 1999; Frank, 2004; Mertl, 1999), but has not yet been successfully utilized in a magnetic delivery method.

A method for weak surface attachment of Bovine Serum Albumin was adapted to 350 nm diameter magnetic particles from the 3-5 µm diameter particles used by the authors (Consigny, et al., 1999). As mentioned above, the particles maintained a carboxyl group per $nm^2$ of surface area. A 1% by volume solution of Bovine Serum Albumin (BSA) (Sigma, Mo.) in Phosphate Buffered Saline (PBS) (Sigma, Mo.) was prepared according to the literature.

Prior to labeling the magnetic particles with albumin, each sample of particles was rinsed 3 times with 70% ethanol, using neodymium permanent magnets for separation between rinses. For every $10^{11}$ particles, 1 mL of BSA/PBS dilution was added to the 15 mL centrifuge tube in which the particles were cleaned. Following the addition of the solution, the sample was gently shaken on a gyrating shaker (Fisher, IL) for 1 hour. After shaking, the particles were separated from the solution using a neodymium permanent magnet, and re-suspended in appropriate volume of culture medium, and stored in a 37° C. water bath (Fisher, IL).

The day before particle preparation, BAECs were routinely cultured as described above, and seeded on 6 tissue culture treated cover slips (25 mm diameter×0.25 mm thick) at a 1:2 split ratio (adjusted to $cm^2$ growth area), and cultured for 1 day to reach confluence. At confluence, all cover slips were seeded with magnetic particles at a $4\times10^3$ particle to cell ratio, using particle preparations as described above. No magnets were placed beneath the cover slips.

24 hours after particle seeding, each cover slip was rinsed three times with warmed culture medium, and submerged in Earle's Balanced Saline Solution (Sigma, Mo.) supplemented with 10% Fetal Bovine Serum (Sigma, Mo.). Each cover slip was imaged fluorescently to assess internalization and cell survival. After imaging, fresh, warm culture medium was added back to each cover slip.

Following imaging, each cover slip was split at a 1:6 split ratio and re-seeded to fresh cover slips. Cells were imaged at 1 hour, monitored for growth over 3 days by a standard phase contrast Nikon microscope (Nikon, Japan), and imaged fluorescently as described above, at 72 hours.

Alternate BAEC samples were prepared as described above, but prepared on glass slides containing 8 wells (0.69 $cm^2$ per well), and labeled with albumin-treated magnetic particles as described above, but at a $2\times10^3$ particle per cell ratio, in order to obtain a clear view of particle internalization and orientation, by confocal microscopy at 60 and 120×. After 24 hours, and particles had been uptaken by the cells, the well covers were removed from the slide, and a drop of Vector-shield Mounting Medium with DAPI (Vector Labs, CA) was applied to each of the 8 cultures, and a cover slip was fixed over the sample with nail polish and allowed to set for 24 hours at 4° C. Confocal imaging was performed on a Leica TCS SP2 Confocal Microscope with Louise Bertrand of the Department of Neurobiology and Anatomy at Drexel University College of Medicine.

An average loading of particles per cell was estimated using the MicroMag Alternating Gradient Magnetometer (AGM) (Princeton Measurements, NJ). BAECs were routinely cultured as described above, and seeded onto nine 5 mm diameter by 0.25 mm thick glass cover slips resting in the bottom of wells in a 48 well plate. Each slip was treated with Rat Tail Type I Collagen as described above. The slips remained in culture for 24 hours until the cells had reached confluence. Cells were loaded with particles by methods as described above, at a loading density of $4\times10^3$ particles per cell. Approximately $8\times10^3$ BAECs can grow upon a 5 mm diameter cover slip. After 24 hours, resting medium was aspirated, the slips were gently rinsed with culture medium three times, top and bottom, following by a gentle alcohol swabbing of the bottom of slip, to remove any particles that may have been attached. Each of slips was then measured for saturation magnetization by AGM. The results were then averaged, and based on the known quantity of cells per slip, used to give an estimate of the average particle loading per cell.

In order to further examine the behavior of BAECs with internalized magnetic particles, studies of calcium response under shear simulation were performed side by side with controls of unlabeled BAECs.

BAECs were routinely cultured as described above, seeded onto 6 tissue culture treated cover slips (25 mm diameter× 0.25 mm thick), and cultured for 1 day to reach 90% confluence. At 90% confluence, 3 cover slips were seeded with magnetic particles at a $4\times10^3$ particle to cell ratio, using particle preparations as described above, the other 3 cover slips.

Endothelial cells were loaded in the dark with fluo3 by incubation with 5 µM Fluo3-acetoxymethyl ester (Molecular Probes, Inc., OR) in Dulbecco's phosphate buffered saline (DPBS) (Sigma, Mo.) at pH 7.4, for 40 minutes at room temperature. The cover slip was then rinsed three times with DPBS before experiments were performed.

For cell shearing experiments, a custom-built controlled cell-shearing device based on a cone and plate configuration was mounted on the microscope stage and used to apply precise mechanical loading conditions to the endothelial cells. For each experiment, a 25 mm diameter cover slip was placed in the circular recess in the plate. Vacuum pressure was applied to hold the cover slip and prevent motion during shear experiment. A volume of 1.5 ml DPBS was added to the well to fill the gap between the cone and plate. For the mechanical loading period, endothelial cells were monitored for about 30 seconds under static conditions prior to the onset of shear stress to establish the basal levels of calcium. Then, the shear stress was ramped up linearly to 20 dyn/cm$^2$ over 0.1 seconds and maintained at a steady level for 5 minutes.

Cell fluorescence was monitored and recorded using a Nikon Diaphot TE300 Eclipse epifluorescent microscope (Optical Apparatus, Inc, PA) with a 20× objective. Fluo3 was excited at 488 nm and emitted fluorescence at wavelength of 515 nm upon binding Ca$^{2+}$. The illumination was controlled by means of an electronic filter wheel (Lambda 10-2, Sutter Instruments Co., CA). The emitted fluorescence passed through a barrier filter and was detected by an intensified CCD digital camera unit (Vedio Scope International, Ltd., VA). The rate of image acquisition was 2 seconds per frame. Prior to the each stimulus, images were recorded for at least 30 seconds. Axon Workbench image acquisition software (Axon Instruments, Inc., CA) was used to acquire fluorescence images and to perform post-acquisition analysis.

Once it was determined that magnetic particles could be delivered to the inside of BAECs, the logical next step was to examine if these magnetic BAECs could be attracted to 316L mesh electroplated with CoNi, under the influence of a magnetic field. This was first demonstrated statically, in sterile cell culture conditions, and then by high flow rate experiments using the parallel plate flow chamber and methods.

For static capture experiments, using the protocol for preparing mesh for cell culture experiments as described above, 5 mm punch-outs of mesh (3 magnetically plated, 3 unplated) were sealed with a thin layer of PDMS onto the center of 25 mm diameter cover slips, followed by cleaning, and coating with collagen. BAECs were routinely cultured in 6 well plates as previously described, and each well was loaded with magnetic particles at a $4\times10^3$ particle per cell ratio. BAECs were allowed to remain in culture for 24 hours for uptake of the magnetic particles.

On the following day, two six-well plates were prepared, one containing the 3 cover slips prepared with magnetic mesh discs, the other containing 3 cover slips with unplated mesh discs. Neodymium pieces, as described above, were mounted beneath each well, and measured to apply an approximately 500 Gauss magnetic field at the center of the mesh. Magnetic BAECs were routinely split and seeded at a 1:2 split ratio to the cover slips and allowed to remain in culture for 30 minutes under the applied field. At 30 minutes, the magnets were removed, and the cover slips were imaged fluorescently. Imaging was also performed at 6 hours, and 24 hours after cell seeding.

For magnetic cell flow experiments, BAECs were routinely cultured on a T75 flask. The flask was loaded with magnetic particles by methods described above, at a seeding rate of $4\times10^3$ particles per cell. BAECs were allowed to remain in culture with the particles for 24 hours to internalize them into the cells. After setting up the flow chamber and magnetic coil under the microscope, the cells were trypsinized routinely, and concentrated in 25 mL of culture medium. The 500 Gauss field was turned on, and the particles were delivered past a 2×2 cm piece of magnetically plated 316L mesh at 15 cm/s flow velocity, followed by a 25 mL rinse with Earle's Balanced Saline Solution (EBSS) (Sigma, Mo.) supplemented with 10% Fetal Bovine Serum (Sigma, Mo.). The field was left on during rinsing. Based on AGM results estimating an average loading-success of approximately $10^3$ particles per cell, the experiments delivered an equivalent number of particles as a concentration 0.25% by volume in the medium. Fluorescent imaging was performed immediately after rinsing.

BAEC cultures were successfully grown atop of PDMS/collagen coated magnetic mesh. The cultures grown on a magnetically plated mesh and an unplated mesh were virtually indistinguishable.

The scarcity of commercially available superparamagnetic particles in the sub-micron diameter scale has resulted in most frequent use of much larger magnetic particles for external labeling. From the performed cell culture studies, 350 nm polystyrene magnetic particles coated with albumin were compartmentalized and uptaken by BAEC cultures. Fluorescent images were taken 24 hours after particle seeding, one hour after re-seeding, and 3 days after re-seeding. Images of BAEC culture with internalized fluorescent magnetic particles taken 24 hours after particle seeding showed expected morphology upon inspection. After imaging at 24 hours the cells were split at a 1 to 6 ratio. Images taken one hour after re-seeding show clear definition of internalized particles around the entire circumference, which attached and spread to culture surfaces as expected from routine cultures. Images taken three days later demonstrate that these internalized particles are being distributed to many of but not all daughter cells. These images indicated that BAECs can survive, re-seed, and divide after the introduction of magnetic particles to cultures.

Figure 7A:
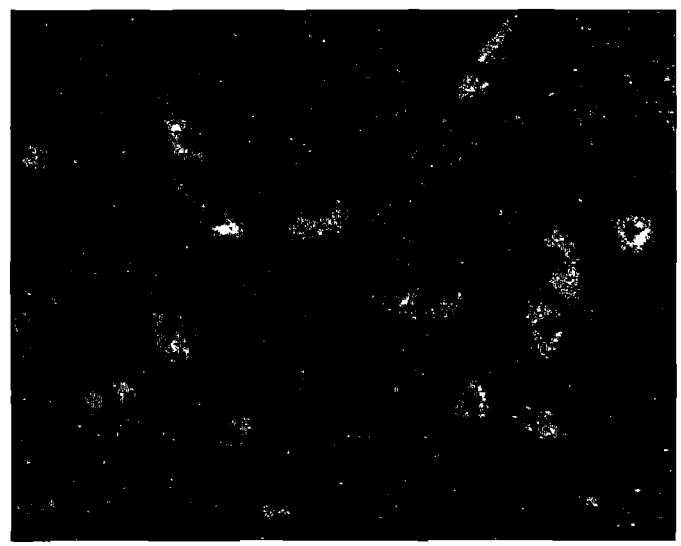
FIG. 7A is an image of BAECs with internalized 350 nm diameter nile red polystyrene magnetizable particles, 1 hour after being passed and re-plated at a 1:6 splitting ratio, shown herein at 20× magnification.
Figure 7B:
FIG. 7B is an image of BAECs with internalized 350 nm diameter nile red polystyrene magnetizable particles, 1 hour after being passed and re-plated at a 1:6 splitting ratio, shown herein at 40× magnification.

FIG. 7A is an image of BAECs with internalized 350 nm diameter nile red polystyrene magnetic particles, 1 hour after being passed and re-plated at a 1:6 splitting ratio at 20× magnification and FIG. 7B is at 40× magnification.

BAEC cultures with internalized magnetic particles (mBAECs) were successfully delivered under static conditions with specificity to the surfaces of a CoNi electroplated 316L mesh. Clearly the mBAECs have been delivered to the areas directly over the wires of the magnetic mesh, while for the unplated mesh sample, the cells were very uniformly distributed across the entire surface. In each case the magnet can influence the rate at which the cells attach to the surface, but without a doubt the magnetic coating of the experimental mesh in combination with the field applied, caused those mBAECs to be captured by the device.

At 6 hours after mBAECs were magnetically delivered to the magnetic mesh, it was observed that many mBAECs had begun to migrate off of the wires into the surrounding area, indicating many cells had survived the magnetic forces used to capture them to the mesh surfaces. At 24 hours, a great many more of the mBAECs have migrated from the area immediately over the wire into the surrounding growth area, and have nearly reached confluence. Clearly, there were still large congregations of cells at the wire intersections, and it was postulated that if great numbers of cells were brought down to these intersections, some cells may have died from isolation from nutrients and proper gas exchange.

Cell flow chamber experiments at roughly 0.25% particle concentration (based on a calculated average particle uptake per cell from AGM analysis) by volume demonstrated the ability to capture mBAECs at high flow velocity in a parallel plate flow chamber. It was expected that these cells could be captured due to an increased susceptibility to magnetic forces due to large particle concentrations in each cell. This experiment indicates that it may be possible to magnetically deliver cells of limited availability, such as stem cells, with increased accuracy and site specificity to a desired location.

The experiments demonstrated that not only do vascular endothelial cells succeed in growth within microns of distance from magnetically plated mesh under the influence of a magnetic field, but can be labeled with magnetic particles, delivered by magnetic force to the surface of the mesh and survive. Attempts by other laboratories have failed at well dispersed and equal loading of magnetic particles into cultures, mainly due to the use of larger particles, but also from their use of applied fields during particle seeding. By placing a permanent magnet underneath the culture continuously during particle seeding to a culture, these particles may have an increased tendency to form chains or large aggregates too large for delivery to the inside of a cell, and may therefore remain on top of the culture. These large aggregates may even be pulled through intracellular space to the bottom of the culture, beneath the cells, but if the field is left in place throughout, one would expect minimal internalization for micron and even large sub-micron particles.

From these experiments, it cannot be assumed that every cell in the initial culture seeded with particles contained them after the introduction to the culture, but it does seem quite likely that many mBAECs distributed particles to daughter cells, and that most cells without particles are daughter cells of the unlabeled cells from the first culture. It was observed that certain cells do seem to maintain the same density of fluorescence seen just after, initial particle introduction. In these cases, the question can be raised on whether or not these mBAECs have undergone mitosis, or were saturated with particles to the point of inhibition. In most cases, by inspection, the culture had a significantly reduced fluorescence per cell, indicating particle transfer during cell division, or release of particles into the surrounding medium during cell division, followed by eventual re-uptake.

Adaptation to other cell cultures, the use of smaller particles, and applications can be determined by those skilled in the art without undue experimentation provided with guidance of this disclosure. The ability to capture mBAECs under high flow makes possible to deliver cells to implants within the body for the purpose of in vivo tissue engineering or wound healing, magnetic cells can also be used as vehicles for drug delivery. When magnitizable particles are introduced into blood flow, they will come in contact with numerous cells and substances, and are particularly vulnerable to immune cell response. By loading cells to saturation with magnetizable particles, the thus formed magnetic cells will have extremely large magnetic susceptibilities, likely raising the capture efficiency significantly while reducing concerns about immune response and blocking of capillaries. In many cases, autologous cell sources could be utilized with ease. If a cell were used solely as a vehicle for drug-loaded particles, its survival would be irrelevant as long as the carriers reached the target site and could effectively transfer therapeutic agents upon arrival. This presents a much more effective method for magnetically targeted drug delivery, making intravenous injection a preferred option, over the current "safe bets" of arterial puncture or catheterization.

Further provided is a method of using the magnetic delivery system for delivery of a therapeutic agent, the method comprising providing the external source of the magnetic field, implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent, and providing an external magnetic field by initializing the external source and thereby (i) magnetizing the magnetizable particle and (ii) increasing the degree of magnetization the magnetizable object and thereby creating the magnetic gradient for attracting and advancing the magnetizable particle toward the magnetizable object, Those skilled in the art would appreciate that magnetizable material have a base line degree of magnetization which is increased in the presence of a magnetic field.

In certain embodiments, the method further comprises administering the magnetizable particle comprising the therapeutic agent to the body and attracting and advancing the magnetizable particle toward the magnetizable object using the magnetic gradient and thereby delivering the therapeutic agent to the location in the body.

In certain embodiments of the method, a size of each segment is selected to commensurate with a size of the magnetizable particle such that at least one spatial dimension of each segment does not exceed by more than about 10,000 times at least one spatial dimension of the magnetizable particle. In certain embodiments of the method, the magnetizable particle is in a form of a superparamagnetic colloidal fluid.

In certain embodiments of the method, the magnetizable particle has a diameter from about 10 nm to about 1000 nm. Preferably, the magnetizable particle has a diameter from 10 nm to 500 nm.

In certain embodiments of the method, the magnetizable object is a member selected from the group consisting of a stent, a pacemaker, a catheter, a tube, a vascular graft, an artificial joint, an artificial bone, a prostate seed, an aneurysm coil, a surgical staple, and a suture.

In certain embodiments of the method, at least one of the magnetizable object and the magnetizable particle is magnetized only in the presence of the external magnetic field. In other embodiments, at least one of the magnetizable object and the magnetizable particle is permanently magnetized.

In certain embodiments of the method, the magnetizable particle comprises a cell such that the magnetizable particle is loaded within a cell and the therapeutic agent is associated with the cell, the magnetizable particle or both.

In certain embodiments of the method, implanting the magnetizable object is accomplished by administering a cluster of gradient forming particles wherein a surface of each gradient forming particle represents a segment of the magnetizable object.

Further provided is a method of using the magnetic delivery system for delivery of a cell to a body, the method comprising providing the external source of the magnetic field, implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent, and administering the magnetizable particle loaded within the cell to the body, providing an external magnetic field by initializing the external source and thereby (i) magnetizing the magnetizable particle and (ii) increasing the degree of magnetization the magnetizable object and thereby creating the magnetic gradient, and attracting and advancing the magnetizable particle toward the magnetizable object using the magnetic gradient and thereby delivering the cell to the location in the body. In certain embodiments of the method, a size of each segment is selected to commensurate with a size of the magnetizable particle such that at least one spatial dimension of each segment does not exceed by more than about 10,000 times at least one spatial dimension (e.g., a width, a height or a diameter) of the magnetizable particle.

Those skilled in the art would appreciate that methods of administration of magnetizable particle or magnetic cells include but not limited to systemic delivery (e.g., by injection, catheterization, etc.).

LIST OF REFERENCES

Babincova, M., Babinec, P. Controlled drug delivery using magnetoliposomes. Cellular & Molecular Biology Letters, vol. 2, pp. 3-7, 1997.

Babincova, M., Babinec, P., Bergemann, C. High-gradient magnetic capture of ferrofluids: implications for drug targeting and tumor embolization. Zeitschrift für Naturforschung, vol. C, pp. 909-911, 2001.

Babincova, M., Babinec, P. A controlled drug delivery system based on degradable magnetic polymers. Pharmazie, vol. 51, pp. 515-516, 1996.

Bakker, D. P., et al. Comparison of Velocity Profiles for Different Flow Chamber Designs Used in Studies of Microbial Adhesion to Surfaces. App. Env. Microbiology, vol. 69(10), pp. 6280-6287, 2003.

Bell G B, Marino A. A., Chesson A. L., Struve F. A. Human sensitivity to weak magnetic fields. The Lancet, 338: 1521-1522 (1991).

Buemi, M., et al. Cell Proliferation/Cell Death Balance in Renal Cell Cultures after Exposure to a Static Magnetic Field. Nephron, vol. 86, pp. 269-273, 2001.

Chen, et al. Internal magnetic device to enhance drug therapy. U.S. Pat. No. 5,921,244, 1999.

Consigny, P. M., Silverberg, D. A., Vitali, N. J. Use of Endothelial Cells Containing Superparamagnetic Microspheres to Improve Endothelial Cell Delivery to Arterial Surfaces after Angioplasty. J. Vasc. Interv. Rad., vol. 10(2), pp. 155-163, 1999.

Dhanikula, A. B., Panchagnula, R. Localized paclitaxel delivery. Int. J. Pharmaceutics, vol. 183, pp. 85-100, 1999.

Duch, M. Electrodeposited Co—Ni alloys for MEMS. J. Micromech. Microeng., vol 12, pp. 400-405, 2002.

Flanders, P. J. An alternating-gradient magnetometer. J. Appl. Phys., vol. 63(8), pp. 3940-3945, 1988.

Flores, G. A. In-vitro blockage of a simulated vascular system using magnetorheological fluids as a cancer therapy. Eur. Cells and Mater., vol. 3, pp. 9-11, 2002.

Forbes, Z. G., Yellen, B. B., Barbee, K. A., Friedman, G. An Approach to Targeted Drug Delivery Based on Uniform Magnetic Fields. IEEE Trans.s on Magn., vol. 39, pp. 3372-3377, 2003.

Frank, J. A., et al. Methods for magnetically labeling stem and other cells for detection by in vivo magnetic resonance imaging. Cytotherapy., vol. 6(6), pp. 621-5, 2004.

Friedlaender, F. J. Particle Motion Near and Capture on Single Spheres in HGMS. IEEE Trans. Magn., vol. Mag-17, no. 6, pp. 2801-2803.

Friedlaender, F. J. Particle Buildup on Single Spheres in HGMS. IEEE Trans. Magn., vol. Mag-17, no. 6, pp. 2804-2806.

Gallo, J. M, Häfeli, U. Correspondence re: A. S. Lübbe et al., Preclinical and clinical experiences with magnetic drug targeting. Cancer Res., vol. 57, pp. 3063-3064, 1997.

Garas, S. M. Overview of therapies for prevention of restenosis after coronary interventions. Pharmacology and Therapeutics, vol. 92, pp. 165-78, 2001.

Garibaldi, et al. Magnetic vascular defect treatment system. U.S. Pat. No. 6,315,709, 2001.

Gershlick, A. H. et al. Treating atherosclerosis: local drug delivery from laboratory studies to clinical trials. Atherosclerosis, vol. 160: 259-71, 2002.

Goodwin, S. C., et al. Single-dose toxicity study of hepatic intra-arterial infusion of doxorubicin coupled to a novel magnetically targeted drug carrier. Toxicological Sciences, vol. 60, pp. 177-183, 2001.

Hanzlik, M., et al. Superparamagnetic magnetite in the upper beak tissue of homing pigeons. BioMetals, vol. 13, pp. 325-331, 2001.

Hehrlein, C. et al. Drug-eluting stent: the 'magic bullet' for prevention of restenosis? Basic Res. Cardiol., vol. 97, pp. 417-23, 2002.

Hilger, I., et al. Evaluation of temperature increase with different amounts of magnetite in liver tissue samples. Invest. Radiol., vol. 32, pp. 705-712, 1997.

Iino, M. Effects of a Homogenous Magnetic Field on Erythrocyte Sedimentation and Aggregation. Bioelectromagnetics, vol. 18, pp. 215-222, 1997.

Illum, L., Church et al. Development of systems for targeting the regional lymph nodes for diagnostic imaging: In vivo behavior of colloidal PEG-coated magnetite nanospheres in the rat following interstitital administration. Pharmaceutical Research, vol. 18, pp. 640-645, 2001.

Kato, T. Encapsulated drugs in targeted cancer therapy. In Bruck S D (Ed.). Controlled drug delivery. CRC Press, Boca Raton, Fla., pp. 190-240, 1983.

Kirschvink J L, Kobayashi-Kirschvink A, Diaz-Ricci J C, and Kirschvink S J. Magnetite in human tissues: A mechanism for the biological effects of weak ELF magnetic fields. Bioelectromagnetics, Suppl. 1: 101-113 (1992).

Kirschvink J L, Kobayashi-Kirschvink A, and Woodford B J. Magnetite biomineralization in the human brain. Proc. Natl. Acad. Sci. USA, 89: 7683-7687 (1992).

Liggins, R. T., Burt, H. M. Paclitaxel loaded poly(L-lactic acid) microspheres: properties of microspheres made with low molecular weight polymers. Int. J. Pharmaceutics, vol. 222, pp. 19-33, 2001.

Lonnemark, M., et al. Effect of superparamagnetic particles as oral contrast medium at magnetic resonance imaging. A phase I clinical study. Acta Radiol., vol. 30(2), pp. 193-196, 1989.

Loweinheim, F. A. Electroplating. New York: McGraw-Hill, 1978.

Lübbe, A. S., Alexiou, C., Bergemann, C. Clinical applications of magnetic drug targeting. J. Surg. Res., vol. 95, pp. 200-206, 2001.

Mertl, M. Magnetic Cells: Stuff or Legend? Science, vol. 283(5403), pp. 775, 1999.

Messer, R. L., et al. Effect of vascular stent alloys on expression of cellular adhesion molecules by endothelial cells. J Long Term Eff Med Implants. vol. 15(1), pp. 39-47, 2005.

Minamimura, T., et al. Tumor regression by inductive hyperthermia combined with hepatic embolization using dextran magnetite-incorporated microspheres in rats. Int. J. Oncology, vol. 16, pp. 1153-1158, 2000.

Mitsumori, M. et al. Targeted hyperthermia using dextran magnetite complex: A new treatment modality for liver tumors. Hepato-Gastroenterology, vol. 43, pp. 1431-1437, 1996.

Moore, L. R., et al. The use of magnetite-doped polymeric microspheres in calibrating cell tracking velocimetry. J. Biochem. Biophys Methods, vol. 44, pp. 115-130, 2000.

Mossbach, K., Schroder, U. Preparation and characterization of magnetic polymers for targeting of drugs. FEBS Letters, vol. 102, pp. 112-116, 1979.

Myung, N. V., et al. Electrodeposited Hard Magnetic Thin Films for MEMS Applications. Proc. Electrochem. Soc., PV, pp. 2000-2029, 2000.

Nakamura T, et al. Magneto-medicine: Biological aspects of ferromagnetic fine particles. J. Appl. Physiol., vol. 42, pp. 1320-1324, 1971.

Ovadia, H., et al. Magnetic microspheres as drug carriers: Factors influencing localization at different anatomical sites in the rats. Isr. J. Med. Sci, vol. 19, pp. 631-637, 1983.

Pauser, S., et al. Liposome-encapsulated superparamagnetic iron oxide particles as markers in an MRI-guided search for tumor-specific drug carriers. Anti-Cancer Drug Design, vol. 12, pp. 125

Plavins, J., Lauva, M. Study of colloidal magnetite-binding erythrocytes: Prospects for cell separation. J. Magn. Mag. Mat., vol. 122, pp. 349-353, 1993.

Regar, E., et al. "Stent development and local drug delivery," Br. Med. Bull., vol. 59, pp. 227-248, 2001.

Rudge, S., et al. Adsorption and desorption of chemotherapeutic drugs from a magnetically targeted carrier (MTC)," J Controlled Release, vol. 74, pp. 335-340, 2001.

Ruuge, E. K., Rusetski, A. N. Magnetic fluids as drug carriers: Targeted transport of drugs by a magnetic field. J. Magn. Mag. Mat., vol. 122, pp. 335-339, 1993.

Sakhnini, L., Khuzaie, R. Magnetic behavior of human erythrocytes at different hemoglobin states. Eur. Biophys. J., vol. 30, pp. 467-470, 2001.

Schenck, J. F. Safety of Strong, Static Magnetic Fields. J. Mag Res. Imaging, vol. 12, pp. 2-19, 2000.

Schewe, H., Takayasu, M., Friendlaender, F. J. Observation of Particle Trajectories in an HGMS Single-Wire System. IEEE Trans. Magn., vol. Mag-16, no. 1, pp. 149-154, 1980.

Schwartz, R. S., et al. Drug-Eluting Stents in Preclinical Studies: Recommended Evaluation From a Consensus Group. Circulation, vol. 106, pp. 1867-73, 2002.

Segre, G., Silberberg, A. Behaviour of macroscopic rigid spheres in Poiseuille flow Part 1 & 2. J. Fluid Mech., vol. 14, pp 115-157, 1962.

Senyei, A., Widder, K., Czerlinski, G. Magnetic guidance of drug-carrying microspheres. J. Appl. Physiol., vol. 49, pp. 3578-3583, 1978.

Singla, A. K., Garg, A., Aggarwal, D. Paclitaxel and its formulations. Int. J. Pharmaceutics, vol. 235, pp. 179-192, 2002.

Sousa, J. E., et al. Use of Rapamycin-Impregnated Stents in Coronary Arteries. Transplantation Proceedings, vol. 35(Suppl. 3A), pp. 165-170S, 2003.

Tiefenauer, L. X., et al. In vivo evaluation of magnetite nanoparticles for use as a tumor contrast agent in MRI. Mag. Res. Imag., vol. 14, pp. 391-402, 1996.

Voltairas, P. A., Fotiadis, D. I., Michalis, L. K. Hydrodynamics of magnetic drug targeting. J. Biomech., vol. 35(6), pp. 813-821, 2002.

Vyas, S. P., Singh, A., Sihorkar, V. Ligand-receptor-mediated drug delivery: an emerging paradigm in cellular drug targeting. Crit. Rev. Ther. Drug Carrier Syst., vol. 18(1), pp. 1-76, 2001.

Wang, J., et al. Characterization of the initial burst release of a model peptide from poly(D, L,-lactide-co-glycolide) microspheres. J. Cont. Rel., vol. 82, pp. 289-307, 2002.

Wang, N., Butler, J. P., Ingber, D. E. Mechanotransduction across the cell surface and through the cytoskeleton. Science, vol. 260(5111), pp. 1124-1127, 1993.

Watarai, H., Namba, M. Capillary magnetophoresis of human blood cells and their magnetphoretic trapping in a flow system. J. Chromatography A, vol. 961, pp. 3-8, 2002.

Widder, K. J., Senyei, A. E., Ranney, D. F. Magnetically responsive microspheres and other carriers for the biophysical targeting of antitumor agents. Advances in Pharmacology and Chemotherapy, vol. 16, pp. 213-271, 1979.

Widder, et al. Method of delivering a therapeutic agent to a target capillary bed. U.S. Pat. No. 4,345,588, 1982.

Xia, Y., Whitesides, G. M. Soft Lithography. Annu. Rev. Mater. Sci., vol. 28, pp. 153-184, 1998.

Yanase, M. Antitumor immunity induction by intracellular hyperthermia using magnetite cationic liposomes. Jap J. Canc. Res., vol. 89, pp. 775-782, 1998.

Yellen, B. B., Forbes, Z. G., Halverson, D. S., Fridman, G., Barbee, K. A., Chorny, M., Levy, R., Friedman, G. Targeted Drug Delivery to Magnetic Implants for Therapeutic Applications. (to be published in Journal of Magnetism and Magnetic Materials May 2005).

Zborowski, M., et al. Red Blood Cell Magnetophoresis. Biophysical Journal, vol. 24, pp. 2683-2645, 2003.

Zhang, Y., Kohler, N., Zhang, M. Surface modification of superparamagnetic magnetite nanoparticles and their intracellular uptake. Biomaterials, vol. 23, pp. 1553-1561, 2002.

What is claimed is:

1. A magnetic delivery system for delivering a magnetizable particle to a location in a body, the magnetic delivery system comprising:
   a magnetizable object, wherein the magnetizable object includes a plurality of segments distributed throughout the magnetizable object and wherein the segments are configured to provide a magnetic gradient for attracting the magnetizable particle; and
   wherein the segments further comprise a coating wherein the coating is patterned to provide non-uniform magnetization of a surface of the segments when the magnetizable object is magnetized; and
   an external source of a magnetic field capable of (i) magnetizing the magnetizable particle and (ii) increasing a degree of magnetization of the magnetizable object and thereby creating the magnetic gradient.

2. The magnetic delivery system of claim 1, wherein a size of each segment is selected to be commensurate with a size of the magnetizable particle such that at least one spatial dimension of each segment does not exceed by more than about 10,000 times at least one spatial dimension of the magnetizable particle.

3. The magnetic delivery system of claim 2, wherein the size of each segment is selected to be commensurate with the size of the magnetizable particle such that at least one spatial dimension of each segment does not exceed by more than about 100 times at least one spatial dimension of the magnetizable particle.

4. The magnetic delivery system of claim 1, wherein the magnetizable object is in the shape of a cylinder, a cylindrical rod, a cube, a cubical rod, a spring, a circular disc, a mesh, a ring, a wire, a sphere or a combination thereof.

5. The magnetic delivery system of claim 1, wherein the magnetizable object is a member selected from the group consisting of a stent, a pacemaker, a catheter, a tube, a vascular graft, an artificial joint, an artificial bone, a prostate seed, an aneurysm coil, a surgical staple, and a suture.

6. The magnetic delivery system of claim 1, wherein the magnetizable object comprises a cluster of gradient forming particles, wherein a surface of each gradient forming particle represents a segment of the magnetizable object.

7. The magnetic delivery system of claim 1, wherein the magnetizable object is made from at least one of materials selected from the group consisting of cobalt, nickel, iron, manganese, samarium and neodymium.

8. The magnetic delivery system of claim 1, wherein the magnetizable object is in a shape of a support made from a metal, a rare earth element, a ceramic, a polymer or a combination thereof.

9. The magnetic delivery system of claim 1, wherein the coating is made from a metal, a rare earth element, a ceramic, a polymer or a combination thereof.

10. The magnetic delivery system of claim 1, wherein the segments comprise patterns of indentations and/or ridges of various length, width, depth and shape.

11. The magnetic delivery system of claim 1, wherein the segments comprise patterns of materials with different degrees of magnetization.

12. The magnetic delivery system of claim 1, further comprising the magnetizable particle.

13. The magnetic delivery system of chum 12, wherein at least one of the magnetizable object and the magnetizable particle is magnetized only in the presence of the external magnetic field.

14. The magnetic delivery system of claim 12, wherein at least one of the magnetizable object and the magnetizable particle is permanently magnetized.

15. The magnetic deliver system of claim 12, wherein the magnetization of at least one of the magnetizable object and the magnetizable particle is increased in the presence of the external magnetic field.

16. The magnetic delivery system of claim 12, wherein the magnetizable particle is in a form of a superparamagnetic colloidal fluid.

17. The magnetic delivery system of claim 12, wherein the magnetizable particle has a diameter of less than 10 micrometers.

18. The magnetic delivery system of claim 12, wherein the magnetizable particle has a diameter from about 10 nm to about 1000 nm.

19. The magnetic delivery system of claim 12, wherein the magnetizable particle has a diameter from 10 nm to 500 nm.

20. The magnetic delivery system of claim 12, wherein the magnetizable particle comprises at least one material selected from the group consisting of $Fe_2O_3$, $Fe_3O_4$, FeNi, FePt, Fe, and CoNi alloy.

21. The magnetic delivery system of claim 12, wherein the magnetizable particle comprises a therapeutic agent.

22. The magnetic delivery system of claim 21, wherein the magnetizable particle is in a form of a superparamagnetic colloidal fluid.

23. The magnetic delivery system of claim 12, wherein the magnetizable particle is loaded within a cell, thereby forming a magnetic cell.

24. The magnetic delivery system of claim 23, wherein the magnetic cell comprises a therapeutic agent, such that the therapeutic agent is associated with the cell, the magnetizable particle or both.

25. A method of using the magnetic delivery system of claim 1 for delivery of a therapeutic agent, the method comprising:
providing the external source of the magnetic field;
implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent; and
providing an external magnetic field by initializing the external source and thereby (i) magnetizing the magnetizable particle and (ii) increasing the degree of magnetization the magnetizable object and thereby creating the magnetic gradient for attracting and advancing the magnetizable particle toward the magnetizable object.

26. The method of claim 25, further comprising:
administering the magnetizable particle comprising the therapeutic agent to the body; and attracting and advancing the magnetizable particle toward the magnetizable object using the magnetic gradient and thereby delivering the therapeutic agent to the location in the body.

27. The method of claim 26, wherein a size of each segment is selected to be commensurate with a size of the magnetizable particle such that at least one spatial dimension of each segment does not exceed by more than about 10,000 times at least one spatial dimension of the magnetizable particle.

28. The method of claim 26, wherein the magnetizable particle is in a form of a superparamagnetic colloidal fluid.

29. The method of claim 26, wherein the magnetizable particle has a diameter from about 10 nm to about 1000 nm.

30. The method of claim 26, wherein the magnetizable particle has a diameter from 10 nm to 500 nm.

31. The method of claim 26, wherein the magnetizable object is a member selected from the group consisting of a stem, a pacemaker, a catheter, a tube, a vascular graft, an artificial joint, an artificial bone, a prostate seed, an aneurysm coil, as surgical staple, and a suture.

32. The method of claim 26, wherein at least one of the magnetizable object and the magnetizable particle is magnetized only in the presence of the external magnetic field.

33. The method of claim 26, wherein at least one of the magnetizable object and the magnetizable particle is permanently magnetized.

34. The method of claim 26, wherein the magnetizable particle comprises a cell such that the magnetizable particle is loaded within a cell and the therapeutic agent is associated with the cell, the magnetizable particle or both.

35. The method of claim 25, wherein implanting the magnetizable object is accomplished by administering a cluster of gradient forming particles wherein a surface of each gradient forming particle represents a segment of the magnetizable object.

36. A method of using the magnetic delivery system of claim 1 for delivery of a cell to a body, the method comprising:
providing the external source of the magnetic field;
implanting the magnetizable object in the body, wherein the magnetizable object includes a plurality of segments distributed throughout the magnetizable object and wherein the segments are configured to provide a magnetic gradient for attracting a magnetizable particle comprising a therapeutic agent;
administering the magnetizable particle loaded within the cell to the body;
providing an external magnetic field by initializing the external source and thereby (i) magnetizing the magnetizable panicle and (ii) increasing the degree of magnetization the magnetizable object and thereby creating the magnetic gradient; and attracting and advancing the magnetizable particle toward the magnetizable object using the magnetic gradient and thereby delivering the cell to the location in the body.

37. The method of chum 36, wherein a size of each segment is selected to be commensurate with a size of the magnetizable particle such that at least one spatial dimension of each segment does not exceed by more than about 10,000 times at least one spatial dimension of the magnetizable particle.

* * * * *